(12) United States Patent
Hansch et al.

(10) Patent No.: US 10,173,963 B2
(45) Date of Patent: *Jan. 8, 2019

(54) QUATERNIZED AMMONIUM SALTS OF HYDROCARBYL EPOXIDES AND USE THEREOF AS ADDITIVES IN FUELS AND LUBRICANTS

(71) Applicant: BASF SE, Ludwigshafen (DE)

(72) Inventors: Markus Hansch, Speyer (DE); Harald Boehnke, Mannheim (DE); Wolfgang Grabarse, Mannheim (DE); Hannah Maria Koenig, Stutensee (DE); Arno Lange, Bad Duerkheim (DE); Ludwig Voelkel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/436,951

(22) PCT Filed: Oct. 23, 2013

(86) PCT No.: PCT/EP2013/072169
§ 371 (c)(1),
(2) Date: Apr. 20, 2015

(87) PCT Pub. No.: WO2014/064151
PCT Pub. Date: May 1, 2014

(65) Prior Publication Data
US 2015/0266808 A1 Sep. 24, 2015

(30) Foreign Application Priority Data
Oct. 23, 2012 (EP) .................................. 12189538

(51) Int. Cl.
*C07C 215/08* (2006.01)
*C10L 1/222* (2006.01)
(Continued)

(52) U.S. Cl.
CPC .......... *C07C 215/08* (2013.01); *C07C 213/04* (2013.01); *C07C 215/40* (2013.01);
(Continued)

(58) Field of Classification Search
CPC ... C07C 215/08; C07C 213/04; C07C 215/40; C10L 1/22; C10L 1/232; C10L 10/06;
(Continued)

(56) References Cited

U.S. PATENT DOCUMENTS 4,171,959 A 10/1979 Vartanian
4,248,719 A 2/1981 Chafetz et al.
(Continued)

FOREIGN PATENT DOCUMENTS

DE 38 26 608 A1 2/1990
DE 38 38 918 A1 5/1990
(Continued)

OTHER PUBLICATIONS

U.S. Appl. No. 13/431,531, filed Mar. 27, 2012, US2012/0251889 A1, Janssen, et al.
(Continued)

*Primary Examiner* — Taiwo Oladapo
(74) *Attorney, Agent, or Firm* — Oblon, McClelland, Maier & Neustadt, L.L.P.

(57) ABSTRACT

The present invention relates to novel quaternized ammonium salts of hydrocarbyl epoxides, to the preparation thereof and to the use thereof as a fuel additive and lubricant additive, such as, more particularly, as a detergent additive; for reducing or preventing deposits in the injection systems of direct injection diesel engines, especially in common rail injection systems, for reducing the fuel consumption of direct injection diesel engines, especially of diesel engines with common rail injection systems, and for minimizing power loss in direct injection diesel engines, especially in (Continued)

diesel engines with common rail injection systems; and as an additive for gasoline fuels, especially for operation of DISI engines.

16 Claims, 1 Drawing Sheet

(51) Int. Cl.

| | |
|---|---|
| C07C 215/40 | (2006.01) |
| C07D 209/12 | (2006.01) |
| C10M 133/44 | (2006.01) |
| C10M 133/54 | (2006.01) |
| C10M 133/58 | (2006.01) |
| C10M 141/06 | (2006.01) |
| C10M 161/00 | (2006.01) |
| C10L 1/14 | (2006.01) |
| C10L 1/232 | (2006.01) |
| C10L 1/2383 | (2006.01) |
| C10L 10/04 | (2006.01) |
| C10L 10/06 | (2006.01) |
| C10M 133/08 | (2006.01) |
| C07C 213/04 | (2006.01) |
| C07D 207/04 | (2006.01) |
| C10L 1/22 | (2006.01) |
| C10L 1/188 | (2006.01) |
| C10L 1/189 | (2006.01) |

(52) U.S. Cl.
CPC ......... *C07D 207/04* (2013.01); *C07D 209/12* (2013.01); *C10L 1/143* (2013.01); *C10L 1/22* (2013.01); *C10L 1/2225* (2013.01); *C10L 1/232* (2013.01); *C10L 1/2383* (2013.01); *C10L 10/04* (2013.01); *C10L 10/06* (2013.01); *C10M 133/08* (2013.01); *C10M 133/44* (2013.01); *C10M 133/54* (2013.01); *C10M 133/58* (2013.01); *C10M 141/06* (2013.01); *C10M 161/00* (2013.01); *C10L 1/189* (2013.01); *C10L 1/1881* (2013.01); *C10L 1/1888* (2013.01); *C10L 1/221* (2013.01); *C10L 2200/0259* (2013.01); *C10L 2270/023* (2013.01); *C10L 2270/026* (2013.01); *C10M 2207/121* (2013.01); *C10M 2207/125* (2013.01); *C10M 2207/144* (2013.01); *C10M 2207/18* (2013.01); *C10M 2215/042* (2013.01); *C10M 2215/223* (2013.01); *C10M 2215/26* (2013.01); *C10M 2215/30* (2013.01); *C10N 2230/04* (2013.01); *C10N 2240/103* (2013.01); *C10N 2240/104* (2013.01)

(58) Field of Classification Search
CPC ........ C10L 10/04; C10L 1/143; C10L 1/2383; C10L 1/2225; C10L 2200/0259; C10L 1/221; C10L 1/1881; C10L 1/189; C10L 1/1888; C10L 2270/023; C10L 2270/026; C07D 207/04; C07D 209/12; C10M 133/44; C10M 133/08; C10M 133/54; C10M 133/58; C10M 141/06; C10M 161/00; C10M 2207/121; C10M 2207/125; C10M 2207/18; C10M 2215/042; C10M 2215/223; C10M 2215/26; C10M 2215/30; C10M 2207/144; C10N 2240/103; C10N 2240/104
See application file for complete search history.

(56) References Cited

U.S. PATENT DOCUMENTS

| | | | |
|---|---|---|---|
| 4,491,455 A | | 1/1985 | Ishizaki et al. |
| 4,621,141 A | * | 11/1986 | Chibnik ............ B01D 37/03 44/332 |
| 4,832,702 A | | 5/1989 | Kummer et al. |
| 4,877,416 A | | 10/1989 | Campbell |
| 4,959,077 A | | 9/1990 | Martischius et al. |
| 5,004,478 A | | 4/1991 | Vogel et al. |
| 5,112,364 A | | 5/1992 | Rath et al. |
| 5,298,039 A | | 3/1994 | Mohr et al. |
| 5,660,601 A | | 8/1997 | Oppenländer et al. |
| 5,746,786 A | | 5/1998 | Mueller et al. |
| 6,069,281 A | | 5/2000 | Kropp et al. |
| 6,140,541 A | | 10/2000 | Melder et al. |
| 6,371,999 B1 | | 4/2002 | Mohr et al. |
| 6,610,797 B1 | | 8/2003 | Deckers et al. |
| 6,743,266 B2 | | 6/2004 | DeRosa et al. |
| 8,629,220 B2 | | 1/2014 | Prusty et al. |
| 8,697,820 B2 | | 4/2014 | Koenig et al. |
| 8,865,858 B2 | | 10/2014 | Lange et al. |
| 9,006,158 B2 | | 4/2015 | Lange et al. |
| 9,023,970 B2 | | 5/2015 | Lange et al. |
| 9,039,791 B2 | | 5/2015 | Peretolchin et al. |
| 2004/0049971 A1 | | 3/2004 | Bernasconi et al. |
| 2004/0077507 A1 | | 4/2004 | Lange et al. |
| 2004/0102653 A1 | | 5/2004 | Lange et al. |
| 2005/0044779 A1 | | 3/2005 | Schwahn et al. |
| 2008/0227922 A1 | | 9/2008 | Rath et al. |
| 2008/0307698 A1 | | 12/2008 | Barton et al. |
| 2009/0282732 A1 | | 11/2009 | Ahlers et al. |
| 2010/0257777 A1 | * | 10/2010 | Sanchez-Riera ........ C10L 1/026 44/388 |
| 2010/0257779 A1 | | 10/2010 | Barton et al. |
| 2012/0137573 A1 | | 6/2012 | Völkel et al. |
| 2012/0142868 A1 | | 6/2012 | König et al. |
| 2012/0144731 A1 | | 6/2012 | Böhnke |
| 2012/0165473 A1 | | 6/2012 | Koenig et al. |
| 2012/0178824 A1 | | 7/2012 | König et al. |
| 2012/0184702 A1 | | 7/2012 | Lange et al. |
| 2012/0222348 A1 | | 9/2012 | Böhnke |
| 2012/0251889 A1 | | 10/2012 | Janssen et al. |
| 2013/0043427 A1 | | 2/2013 | Cox et al. |
| 2013/0098609 A1 | | 4/2013 | Oetter et al. |
| 2013/0102748 A1 | | 4/2013 | Koenig et al. |
| 2013/0133243 A1 | | 5/2013 | Röger-Göpfert et al. |
| 2013/0189550 A1 | | 7/2013 | Janssen et al. |
| 2013/0205654 A1 | | 8/2013 | Peretolchin et al. |
| 2013/0225463 A1 | | 8/2013 | Hansch et al. |
| 2013/0228332 A1 | | 9/2013 | Maitro-Vogel et al. |
| 2013/0232858 A1 | | 9/2013 | Strittmatter et al. |
| 2013/0276362 A1 | | 10/2013 | Boehnke |
| 2013/0296210 A1 | | 11/2013 | Hansch et al. |
| 2013/0341559 A1 | | 12/2013 | Lange et al. |
| 2014/0017411 A1 | | 1/2014 | Lange et al. |
| 2014/0020285 A1 | | 1/2014 | Voelkel et al. |
| 2014/0034004 A1 | | 2/2014 | Walter et al. |
| 2014/0094561 A1 | | 4/2014 | Lange et al. |
| 2015/0152349 A1 | | 6/2015 | Lange et al. |

FOREIGN PATENT DOCUMENTS

| | | |
|---|---|---|
| DE | 41 42 241 A1 | 6/1993 |
| DE | 43 09 074 | 9/1994 |
| DE | 196 20 262 A1 | 11/1997 |
| DE | 101 02 913 A1 | 7/2002 |
| DE | 10 2005 041 789 A1 | 3/2007 |
| EP | 0 061 895 A2 | 10/1982 |
| EP | 0 244 616 A2 | 11/1987 |
| EP | 0 261 957 A2 | 3/1988 |
| EP | 0 307 815 A1 | 3/1989 |
| EP | 0 310 875 A1 | 4/1989 |
| EP | 0 356 725 A1 | 3/1990 |
| EP | 0 452 328 A1 | 10/1991 |
| EP | 0 476 485 A1 | 3/1992 |
| EP | 0 548 617 A2 | 6/1993 |

(56) References Cited

FOREIGN PATENT DOCUMENTS

| | | |
|---|---|---|
| EP | 0 639 632 A1 | 2/1995 |
| EP | 0 700 985 A1 | 3/1996 |
| EP | 0 831 141 A1 | 3/1998 |
| EP | 1 422 246 A2 | 5/2004 |
| EP | 2 033 945 A1 | 3/2009 |
| WO | WO 87/01126 A1 | 2/1987 |
| WO | WO 91/03529 A1 | 3/1991 |
| WO | WO 93/18115 A1 | 9/1993 |
| WO | WO 94/21754 | 9/1994 |
| WO | WO 94/24231 A1 | 10/1994 |
| WO | WO 96/03367 A1 | 2/1996 |
| WO | WO 96/03479 A1 | 2/1996 |
| WO | WO 97/03946 A1 | 2/1997 |
| WO | WO 98/04656 A1 | 2/1998 |
| WO | WO 99/29748 A1 | 6/1999 |
| WO | WO 00/44857 A1 | 8/2000 |
| WO | WO 00/47698 A1 | 8/2000 |
| WO | WO 2004/035715 A1 | 4/2004 |
| WO | WO 2005/054314 A2 | 6/2005 |
| WO | WO 2006/135881 A2 | 12/2006 |
| WO | WO 2007/025700 A1 | 3/2007 |
| WO | WO 2008/060888 A2 | 5/2008 |

OTHER PUBLICATIONS

U.S. Appl. No. 13/307,392, filed Nov. 30, 2011, US2012/0137573 A1, Völkel, et al.
U.S. Appl. No. 14/032,889, filed Sep. 20, 2013, US2014/0020285 A1, Voelkel, et al.
U.S. Appl. No. 13/315,468, filed Dec. 9, 2011, US2012/0144731 A1, Böhnke.
U.S. Appl. No. 13/407,422, filed Feb. 28, 2012, US2012/0222348 A1, Böhnke.
U.S. Appl. No. 13/535,847, filed Jun. 28, 2012, US2013/0133243 A1, Röger-Göpfert, et al.
U.S. Appl. No. 13/305,283, filed Nov. 28, 2011, US2012/0142868 A1, König, et al.
U.S. Appl. No. 13/347,255, filed Jan. 10, 2012, US2012/0178824 A1, König, et al.
U.S. Appl. No. 13/353,780, filed Jan. 19, 2012, US2012/0184702 A1, Lange, et al.
U.S. Appl. No. 13/305,132, filed Nov. 28, 2011, US2012/0165473 A1, Koenig, et al.
U.S. Appl. No. 14/619,171, filed Feb. 11, 2015, US2015/0152349 A1, Lange, et al.
U.S. Appl. No. 13/655,839, filed Oct. 19, 2012, US2013/0102748 A1, Koenig, et al.
U.S. Appl. No. 13/940,835, filed Jul. 12, 2013, US2014/0017411 A1, Lange, et al.
U.S. Appl. No. 13/748,243, filed Jan. 23, 2013, US2013/0189550 A1, Janssen, et al.
U.S. Appl. No. 13/653,946, filed Oct. 17, 2012, US2013/0098609 A1, Oetter, et al.
U.S. Appl. No. 13/712,297, filed Dec. 12, 2012, US2013/0296210 A1, Hansch, et al.
U.S. Appl. No. 13/781,929, filed Mar. 1, 2013, US2013/0232858 A1, Strittmatter, et al.
U.S. Appl. No. 13/587,055, filed Aug. 16, 2012, US2013/0043427 A1, Cox, et al.
U.S. Appl. No. 14/038,947, filed Sep. 27, 2013, US2014/0094561 A1, Lange, et al.
U.S. Appl. No. 13/761,644, filed Feb. 7, 2013, US2013/0205654 A1, Peretolchin, et al.
U.S. Appl. No. 13/668,985, filed Nov. 5, 2012, US2013/0225463 A1, Hansch, et al.
U.S. Appl. No. 13/683,618, filed Nov. 21, 2012, US2013/0228332 A1, Maitro-Vogel, et al.
U.S. Appl. No. 13/923,715, filed Jun. 21, 2013, US2013/0341559 A1, Lange, et al.
U.S. Appl. No. 13/783,708, filed Mar. 4, 2013, Strittmatter, et al.
U.S. Appl. No. 13/866,291, filed Apr. 19, 2013, US2013/0276362 A1, Boehnke.
U.S. Appl. No. 14/678,339, filed Apr. 3, 2015, Peretolchin, et al.
U.S. Appl. No. 13/953,900, filed Jul. 30, 2013, US2014/0034004 A1, Walter, et al.
International Preliminary Report on Patentability dated Apr. 23, 2015 in PCT/EP2013/072169 filed on Oct. 23, 2013 (English translation only).
International Search Report dated Dec. 12, 2013 in PCT/EP2013/072169 filed on Oct. 23, 2013.

\* cited by examiner

| step | duration (minutes) | engine speed (rpm) +/- 20 | load (%) | torque (Nm) +/- 5 | boost air after IC (°C) +/- 3 |
|---|---|---|---|---|---|
| 1 | 2' | 1750 | (20) | 62 | 45 |
| 2 | 7' | 3000 | (60) | 173 | 50 |
| 3 | 2' | 1750 | (20) | 62 | 45 |
| 4 | 7' | 3500 | (80) | 212 | 50 |
| 5 | 2' | 1750 | (20) | 62 | 45 |
| 6 | 10' | 4000 | 100 | * | 50 |
| 7 | 2' | 1250 | (10) | 25 | 43** |
| 8 | 7' | 3000 | 100 | * | 50 |
| 9 | 2' | 1250 | (10) | 25 | 43** |
| 10 | 10' | 2000 | 100 | * | 50 |
| 11 | 2' | 1250 | (10) | 25 | 43** |
| 12 | 7' | 4000 | 100 | * | 50 |
| | Σ= 1 hour | | | | |
\* for expected range see appendix 06.5
\*\* target only
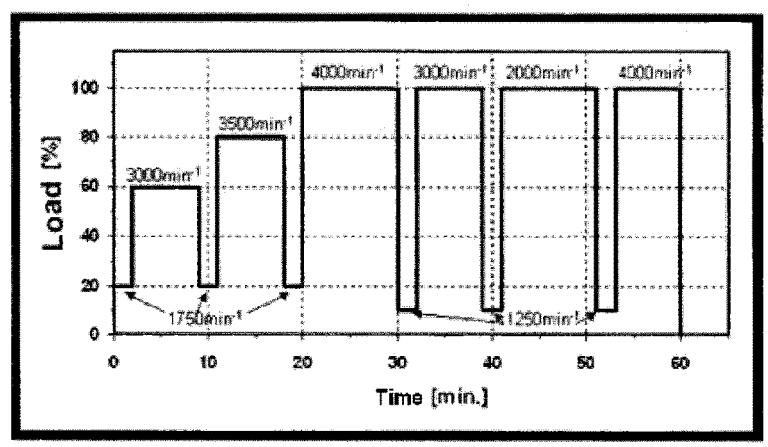

QUATERNIZED AMMONIUM SALTS OF HYDROCARBYL EPOXIDES AND USE THEREOF AS ADDITIVES IN FUELS AND LUBRICANTS

RELATED APPLICATION

This application is a national stage entry of PCT/EP2013/072169, filed Oct. 23, 2013, which claims priority from Europeant Patent Office Application EP 12189538, filed Oct. 23, 2012, which are incorporated by reference in their entirety.

The present invention relates to novel quaternized ammonium salts of hydrocarbyl epoxides, to the preparation thereof and to the use thereof as a fuel additive and lubricant additive, such as, more particularly, as a detergent additive; for reducing or preventing deposits in the injection systems of direct injection diesel engines, especially in common rail injection systems, for reducing the fuel consumption of direct injection diesel engines, especially of diesel engines with common rail injection systems, and for minimizing power loss in direct injection diesel engines, especially in diesel engines with common rail injection systems; and as an additive for gasoline fuels, especially for operation of DISI engines.

STATE OF THE ART

In direct injection diesel engines, the fuel is injected and distributed ultrafinely (nebulized) by a multihole injection nozzle which reaches directly into the combustion chamber of the engine, instead of being introduced into a prechamber or swirl chamber as in the case of the conventional (chamber) diesel engine. The advantage of direct injection diesel engines lies in their high performance for diesel engines and nevertheless low fuel consumption. Moreover, these engines achieve a very high torque even at low speeds.

At present, essentially three methods are being used for injection of the fuel directly into the combustion chamber of the diesel engine: the conventional distributor injection pump, the pump-nozzle system (unit-injector system or unit-pump system), and the common rail system.

In the common rail system, the diesel fuel is conveyed by a pump with pressures up to 2000 bar into a high-pressure line, the common rail. Proceeding from the common rail, branch lines run to the different injectors which inject the fuel directly into the combustion chamber. The full pressure is always applied to the common rail, which enables multiple injection or a specific injection form. In the other injection systems, in contrast, only a smaller variation in the injection is possible. Injection in the common rail is divided essentially into three groups: (1.) pre-injection, by which essentially softer combustion is achieved, such that harsh combustion noises ("nailing") are reduced and the engine seems to run quietly; (2.) main injection, which is responsible especially for a good torque profile; and (3.) post-injection, which especially ensures a low $NO_x$ value. In this post-injection, the fuel is generally not combusted, but instead vaporized by residual heat in the cylinder. The exhaust gas/fuel mixture formed is transported to the exhaust gas system, where the fuel, in the presence of suitable catalysts, acts as a reducing agent for the nitrogen oxides $NO_x$.

The variable, cylinder-individual injection in the common rail injection system can positively influence the pollutant emission of the engine, for example the emission of nitrogen oxides ($NO_x$), carbon monoxide (CO) and especially of particulates (soot). This makes it possible, for example, for engines equipped with common rail injection systems to meet the Euro 4 standard theoretically even without additional particulate filters.

In modern common rail diesel engines, under particular conditions, for example when biodiesel-containing fuels or fuels with metal impurities such as zinc compounds, copper compounds, lead compounds and other metal compounds are used, deposits can form on the injector orifices, which adversely affect the injection performance of the fuel and hence impair the performance of the engine, i.e. especially reduce the power, but in some cases also worsen the combustion. The formation of deposits is enhanced further by further developments in the injector construction, especially by the change in the geometry of the nozzles (narrower, conical orifices with rounded outlet). For lasting optimal functioning of engine and injectors, such deposits in the nozzle orifices must be prevented or reduced by suitable fuel additives.

In the injection systems of modern diesel engines, deposits cause significant performance problems. It is common knowledge that such deposits in the spray channels can lead to a decrease in the fuel flow and hence to power loss. Deposits at the injector tip, in contrast, impair the optimal formation of fuel spray mist and, as a result, cause worsened combustion and associated higher emissions and increased fuel consumption. In contrast to these conventional "external" deposition phenomena, "internal" deposits (referred to collectively as internal diesel injector deposits (IDID)) in particular parts of the injectors, such as at the nozzle needle, at the control piston, at the valve piston, at the valve seat, in the control unit and in the guides of these components, also increasingly cause performance problems. Conventional additives exhibit inadequate action against these IDIDs.

U.S. Pat. No. 4,248,719 describes quaternized ammonium salts which are prepared by reacting an alkenylsuccinimide with a monocarboxylic ester and find use as dispersants in lubricant oils for prevention of sludge formation. More particularly, for example, the reaction of polyisobutylsuccinic anhydride (PIBSA) with N,N-dimethylaminopropylamine (DMAPA) and quaternization with methyl salicylate is described. However, use in fuels, more particularly diesel fuels, is not proposed therein.

U.S. Pat. No. 4,171,959 describes quaternized ammonium salts of hydrocarbyl-substituted succinimides, which are suitable as detergent additives for gasoline fuel compositions. Quaternization is preferably accomplished using alkyl halides. Also mentioned are organic $C_2$-$C_8$-hydrocarbyl carboxylates and sulfonates. Consequently, the quaternized ammonium salts provided according to the teaching therein have, as a counterion, either a halide or a $C_2$-$C_8$-hydrocarbyl carboxylate or a $C_2$-$C_8$-hydrocarbyl sulfonate group.

EP-A-2 033 945 discloses cold flow improvers which are prepared by quaternizing specific tertiary monoamines bearing at least one $C_8$-$C_{40}$-alkyl radical with a $C_1$-$C_4$-alkyl ester of specific carboxylic acids. Examples of such carboxylic esters are dimethyl oxalate, dimethyl maleate, dimethyl phthalate and dimethyl fumarate. Uses other than that for improvement of the CFPP value of middle distillates are not demonstrated in EP-A-2 033 945.

WO 2006/135881 describes quaternized ammonium salts prepared by condensation of a hydrocarbyl-substituted acylating agent and of an oxygen or nitrogen atom-containing compound with a tertiary amino group, and subsequent quaternization by means of hydrocarbyl epoxide in combination with stoichiometric amounts of an acid such as, more particularly, acetic acid. Further quaternizing agents claimed in WO 2006/135881 are dialkyl sulfates, benzyl halides and hydrocarbyl-substituted carbonates, and dimethyl sulfate, benzyl chloride and dimethyl carbonate have been studied experimentally.

WO 2008/060888 discloses quaternary ammonium salts of polyalkene-substituted amines which are used as detergent additives in fuel compositions for reduction of intake system deposits. Preferred compounds are prepared by hydroformylation of polyisobutene or chlorination of polyisobutene and subsequent reaction with a diamine, followed by the quaternization of the polyisobutenediamine thus obtained by means of conventional quaternizing agents, such as dimethyl sulfate, benzyl chloride, or styrene epoxide/acid.

The quaternized compounds known to date are preparable with a relatively high level of synthesis complexity. It was therefore an object of the present invention to provide quaternized fuel additives which are firstly easier to prepare and secondly have satisfactory additive properties.

BRIEF DESCRIPTION OF THE INVENTION

It has now been found that, surprisingly, the above object is achieved by providing quaternized ammonium salts of hydrocarbyl epoxides and fuel compositions and lubricant compositions additized therewith.

Surprisingly, the inventive additives, as illustrated especially by the appended use examples, are not just preparable in a simple manner from the corresponding hydrocarbyl epoxide precursors, but also surprisingly exhibit satisfactory additive properties, such as, more particularly, in operation in modern diesel engines.

DESCRIPTION OF FIGURES

FIG. 1 shows the running of the one-hour engine test cycle according to CEC F-098-08.

DETAILED DESCRIPTION OF THE INVENTION

A1) Specific Embodiments

The present invention relates especially to the following embodiments:

1. A fuel composition or lubricant composition comprising, in a majority of a customary fuel or lubricant, an effective proportion of at least one reaction product comprising a quaternized nitrogen compound, or a fraction thereof which comprises a quaternized nitrogen compound and is obtained from the reaction product by purification, said reaction product being obtainable by reacting at least one hydrocarbyl epoxide of the general formula I

(I)

in which
at least one of the $R_1$ and $R_2$ radicals is a straight-chain or branched, saturated or unsaturated, long-chain hydrocarbyl radical, e.g. polyalkylene radical, and the other of the two radicals is optionally H or a short-chain hydrocarbyl radical (especially $C_1$-$C_4$ alkyl); and the $R_3$ and $R_4$ radicals are the same or different and are each H or a short-chain hydrocarbyl radical (especially $C_1$-$C_4$ alkyl);
with at least one tertiary amine of the general formula II

in which
$R_a$, $R_b$ and $R_c$ are each independently a straight-chain or branched, saturated or unsaturated, optionally substituted hydrocarbyl radical, especially short-chain hydrocarbyl radical, or alkyl or alkenyl, especially $C_1$-$C_{24}$-alkyl or $C_2$-$C_{24}$-alkenyl, or two of the $R_a$, $R_b$ and $R_c$ radicals, together with the nitrogen atom to which they are bonded, form an optionally substituted heterocyclic ring, especially 5- to 7-membered, saturated or unsaturated, nonaromatic or aromatic heterocyclic ring, which may optionally bear at least one further ring heteroatom such as O, S or N;
and in the presence of at least one acid of the formula III

in which
$A^-$ is the anion of at least one mono- or polybasic, inorganic or organic, natural or synthetic acid.
The quaternized nitrogen compound may be derived either from a single epoxide of the formula I or a mixture of a plurality of different epoxides of the formula I.

2. The fuel composition or lubricant composition according to embodiment 1, wherein the reaction product comprises at least one compound of the general formula IV

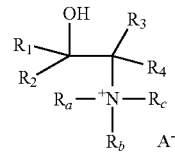

(IV)

in which
the $R_1$, $R_2$, $R_3$, $R_4$, $R_a$, $R_b$, $R_c$ and A radicals are each as defined above.

3. The fuel composition or lubricant composition according to either of embodiments 1 and 2, wherein the amine of the general formula II is selected from tri-$C_1$-$C_{24}$- or tri-$C_4$-$C_{12}$-alkylamines or compounds of the general formula II in which one of the $R_a$, $R_b$ and $R_c$ radicals is a $C_1$-$C_4$-alkyl radical and the two other radicals, together with the nitrogen atom to which they are bonded, form a 5- or 6-membered heterocyclic saturated or unsaturated ring which may optionally bear at least one further ring heteroatom such as O, S or N.

4. The fuel composition or lubricant composition according to any of the preceding embodiments, wherein the compound of the general formula I is a polyalkylene epoxide which is obtained by epoxidizing a polyalkene, especially poly-($C_2$-$C_6$)-alkene, having a number-average molecular weight ($M_n$) of 85 to 20 000, for example 113 to 10 000, or 200 to 10 000 or 350 to 5000, for example 350 to 3000, 500 to 2500, 700 to 2500, or 800 to 1500.

5. The fuel composition or lubricant composition according to any of embodiments 1 to 3, wherein the long-chain hydrocarbyl radical in the compounds of the general formula I is a straight-chain or branched aliphatic hydrocarbyl radical having 8 to 40, especially 10 to 20, 10 to 16 or 10 to 14 connected carbon atoms. Examples include $C_{12}$-$C_{16}$-alkyl epoxides. Especially suitable compounds are those which bear terminal epoxide groups, i.e. two adjacent carbon atoms at the chain end (omega position) or in the omega-1 or omega-2 position bear the epoxide group.

6. The fuel composition or lubricant composition according to embodiment 4, wherein the polyalkylene is a polyisobutene having a proportion of vinylidene double bonds of greater than 70 mol %, especially greater than 80 mol % or greater than 85 mol %.

7. The fuel composition or lubricant composition according to any of the preceding embodiments, selected from diesel fuels, biodiesel fuels, gasoline fuels, and alkanol-containing gasoline fuels.

8. A quaternized nitrogen compound comprising a reaction product as defined in any of embodiments 1 to 5, especially a compound of the formula IV.

9. A quaternized nitrogen compound of the above general formula IV.

10. A process for preparing a quaternized nitrogen compound according to embodiment 7 or 8, comprising the reaction of at least one hydrocarbyl epoxide of the general formula I

(I)

in which
at least one of the $R_1$ and $R_2$ radicals is a straight-chain or branched, saturated or unsaturated, long-chain hydrocarbyl radical, e.g. polyalkylene radical, and the other of the two radicals is optionally H or a short-chain hydrocarbyl radical (especially $C_1$-$C_4$ alkyl); and
the $R_3$ and $R_4$ radicals are the same or different and are each H or a short-chain hydrocarbyl radical (especially $C_1$-$C_4$ alkyl);
with at least one tertiary amine of the general formula II $$R_aR_bR_cN \qquad (II)$$

in which
$R_a$, $R_b$ and $R_c$ are each independently a straight-chain or branched, saturated or unsaturated, optionally substituted hydrocarbyl radical, especially short-chain hydrocarbyl radical, or alkyl or alkenyl, especially $C_1$-$C_{24}$-alkyl or $C_2$-$C_{24}$-alkenyl, or two of the $R_a$, $R_b$ and $R_c$ radicals, together with the nitrogen atom to which they are bonded, form an optionally substituted heterocyclic ring, especially 5- to 7-membered, saturated or unsaturated, nonaromatic or aromatic heterocyclic ring, which may optionally bear at least one further ring heteroatom such as O, S or N;
and in the presence of an acid of the formula III

(III)

in which
$A^-$ is the anion of at least one mono- or polybasic, inorganic or organic, natural or synthetic acid.

11. The process according to embodiment 10, wherein the reaction product comprises at least one compound of the general formula IV

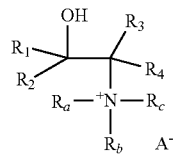

in which
the $R_1$, $R_2$, $R_3$, $R_4$, $R_a$, $R_b$, $R_c$ and A radicals are each as defined above.

12. The process according to either of embodiments 10 and 11, wherein the amine of the general formula II is selected from tri-$C_1$-$C_{24}$- or tri-$C_4$-$C_{12}$-alkylamines or compounds of the general formula II in which one of the $R_a$, $R_b$ and $R_c$ radicals is a $C_1$-$C_4$-alkyl radical and the two other radicals, together with the nitrogen atom to which they are bonded, form a 5- or 6-membered heterocyclic saturated or unsaturated ring which may optionally bear at least one further ring heteroatom such as O, S or N.

13. The process according to any of the preceding embodiments, wherein the compound of the general formula I is a polyalkylene epoxide which is obtained by epoxidizing a polyalkene, especially poly-($C_2$-$C_6$)-alkene, having a number-average molecular weight ($M_n$) of 85 to 20 000, for example 113 to 10 000, or 200 to 10 000 or 350 to 5000, for example 350 to 3000, 500 to 2500, 700 to 2500, or 800 to 1500.

14. The process according to embodiment 13, wherein the polyalkylene is a polyisobutene having a proportion of vinylidene double bonds of greater than 70 mol %, especially greater than 80 mol % or greater than 85 mol %.

15. The use of a quaternized nitrogen compound according to claim 8 or 9 or prepared according to any of embodiments 10 to 14 as a fuel additive or lubricant additive.

16. The use according to embodiment 15 as an additive for reducing the fuel consumption of direct injection diesel engines, especially of diesel engines with common rail injection systems, and/or for minimizing power loss in direct injection diesel engines, especially in diesel engines with common rail injection systems, determined as described in general terms in the experimental section (KC power loss or DU power loss or DU,CU power loss).

17. The use according to embodiment 16 as a gasoline fuel additive for reducing deposits in the intake system of a gasoline engine, such as, more particularly, DISI and PFI (port fuel injector) engines.

18. The use according to embodiment 17 as a diesel fuel additive for reducing and/or preventing deposits in the intake systems, such as especially the internal diesel injector deposits (IDIDs), and/or valve sticking in direct injection diesel engines, especially in common rail injection systems, each determined as described in general terms in the experimental section (XUD-9 or IDIDI).

19. An additive concentrate comprising, in combination with further diesel fuel additives or gasoline fuel additives or lubricant additives, at least one quaternized nitrogen compound as defined in embodiment 8 or 9 or prepared according to any of embodiments 10 to 14.

A2) General Definitions

In the absence of statements to the contrary, the following general conditions apply:

"Hydrocarbyl" can be interpreted widely and comprises both long-chain and short-chain, cyclic and acyclic, straight-chain and branched, saturated and unsaturated, aliphatic, cycloaliphatic and aromatic (e.g. aryl), especially aliphatic, hydrocarbyl radicals having 1 to 50 carbon atoms, which may optionally additionally comprise heteroatoms, for example O, N, NH, S, in the chain thereof.

"Long-chain" hydrocarbyl radicals are straight-chain or branched hydrocarbyl radicals and have 7 to 50 or 8 to 40 or 10 to 20 carbon atoms, which may optionally additionally comprise heteroatoms, for example O, N, NH, S, in the chain thereof. In a particular embodiment, no heteroatoms are present. In addition, the radicals may be mono- or polyunsaturated and have one or more noncumulated, for example 1 to 5, such as 1, 2 or 3, C—C double bonds or C—C triple bonds, especially 1, 2 or 3 double bonds. They may be of natural or synthetic origin. They may also have a number-average molecular weight ($M_n$) of 85 to 20 000, for example 113 to 10 000, or 200 to 10 000 or 350 to 5000, for example 350 to 3000, 500 to 2500, 700 to 2500, or 800 to 1500. In that case, they are more particularly formed essentially from $C_{2-6}$, especially $C_{2-4}$, monomer units such as ethylene, propylene, n- or isobutylene or mixtures thereof, where the different monomers may be copolymerized in random distribution or as blocks. Such long-chain hydrocarbyl radicals are also referred to as polyalkylene radicals or poly-$C_{2-6}$- or poly-$C_{2-4}$-alkylene radicals. Suitable long-chain hydrocarbyl radicals and the preparation thereof are also described, for example, in WO 2006/135881 and the literature cited therein.

Examples of particularly useful polyalkylene radicals are polyisobutenyl radicals derived from what are called "high-reactivity" polyisobutenes which feature a high content of terminal double bonds. Terminal double bonds are alpha-olefinic double bonds of the formula V

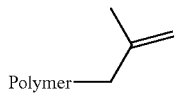

(V)

which are also referred to collectively as vinylidene double bonds. Suitable high-reactivity polyisobutenes are, for example, polyisobutenes which have a proportion of vinylidene double bonds of greater than 70 mol %, especially greater than 80 mol % or greater than 85 mol %. Preference is given especially to polyisobutenes which have homogeneous polymer skeletons. Homogeneous polymer skeletons are possessed especially by those polyisobutenes formed from isobutene units to an extent of at least 85% by weight, preferably to an extent of at least 90% by weight and more preferably to an extent of at least 95% by weight. Such high-reactivity polyisobutenes preferably have a number-average molecular weight within the abovementioned range. In addition, the high-reactivity polyisobutenes may have a polydispersity in the range from 1.05 to 7, especially of about 1.1 to 2.5, for example of less than 1.9 or less than 1.5. Polydispersity is understood to mean the quotient of weight-average molecular weight Mw divided by the number-average molecular weight Mn.

Particularly suitable high-reactivity polyisobutenes are, for example, the Glissopal brands from BASF SE, especially Glissopal 1000 (Mn=1000), Glissopal V 33 (Mn=550) and Glissopal 2300 (Mn=2300), and mixtures thereof. Other number-average molecular weights can be established in a manner known in principle by mixing polyisobutenes of different number-average molecular weights or by extractive enrichment of polyisobutenes of particular molecular weight ranges.

"Short-chain hydrocarbyl" or "low molecular weight hydrocarbyl" represents especially straight-chain or branched $C_1$-$C_7$-alkyl or $C_2$-$C_7$-alkenyl, optionally interrupted by one or more, for example 2, 3 or 4, heteroatom groups such as —O— or —NH—, or optionally mono- or polysubstituted, for example di-, tri- or tetrasubstituted.

"Hydrocarbylene" represents straight-chain or singly or multiply branched bridge groups having 1 to 10 carbon atoms, optionally interrupted by one or more, for example 2, 3 or 4, heteroatom groups such as —O— or —NH—, or optionally mono- or polysubstituted, for example di-, tri- or tetrasubstituted.

"Alkyl" or "lower alkyl" represents especially saturated, straight-chain or branched hydrocarbyl radicals having 1 to 4, 1 to 5, 1 to 6, 1 to 7, 1 to 10, 1 to 16 or 1 to 24 carbon atoms, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; and also n-heptyl, n-octyl, n-nonyl, n-decyl, n-undecyl, n-tridecyl, n-tetradecyl, n-pentadecyl and n-hexadecyl, octadecyl, docosanyl, and the singly or multiply branched analogs thereof. "Lower alkyl" represents especially radicals having 1 to 4, 1 to 5, 1 to 6, or 1 to 7 carbon atoms.

"Hydroxyalkyl" represents especially the mono- or polyhydroxy-substituted, especially mono-hydroxy-substituted, analogs of above alkyl or lower alkyl groups.

"Alkenyl" represents mono- or polyunsaturated, especially monounsaturated, straight-chain or branched hydrocarbyl radicals having 2 to 4, 2 to 6, 2 to 7, 2 to 10, 2 to 16 or 2 to 24 carbon atoms and a double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2- methyl-1-propenyl and 1-ethyl-2-methyl-2-propenyl, and also, where unspecified, the monounsaturated analogs of the above alkyl radicals. "Lower alkenyl" represents especially radicals having 2 to 4, 2 to 5, 2 to 6, or 2 to 7 carbon atoms.

"Alkylene" represents straight-chain or singly or multiply branched hydrocarbyl bridge groups having 1 to 10 or 2 to 6 carbon atoms, for example $C_1$-$C_7$- or $C_2$-$C_6$-alkylene groups selected from —$CH_2$—, —$(CH_2)_2$—, —$(CH_2)_3$—, —$CH_2$—$CH(CH_3)$—, —$CH(CH_3)$—$CH_2$—, —$(CH_2)_4$—, —$(CH_2)_2$—$CH(CH_3)$—, —$CH_2$—$CH(CH_3)$—$CH_2$—, —$(CH_2)_4$—, —$(CH_2)_5$—, —$(CH_2)_6$—, —$(CH_2)_7$—, —CH($CH_3$)—$CH_2$—$CH_2$—$CH(CH_3)$— or —$CH(CH_3)$—$CH_2$—$CH_2$—$CH_2$—$CH(CH_3)$— or $C_1$-$C_4$- or $C_2$-$C_4$-alkylene groups selected from —$CH_2$—, —$(CH_2)_2$—, —$(CH_2)_3$—, —$CH_2$—$CH(CH_3)$—, —$CH(CH_3)$—$CH_2$, —$(CH_2)_4$—, —$(CH_2)_2$—$CH(CH_3)$—, —$CH_2$—$CH(CH_3)$—$CH_2$—.

"Alkenylene" represents the mono- or polyunsaturated, especially monounsaturated, analogs of the above alkylene groups having 2 to 10 carbon atoms, especially $C_2$-$C_7$-alkenylenes or $C_2$-$C_4$-alkenylene, such as —CH=CH—, —CH=CH—$CH_2$—,—$CH_2$—CH=CH—, —CH=CH—$CH_2$—$CH_2$—, —$CH_2$—CH=CH—$CH_2$—, —$CH_2$—$CH_2$—CH=CH—, —$CH(CH_3)$—CH=CH—, —$CH_2$—C($CH_3$)=CH—.

"Cycloalkyl" represents carbocyclic radicals having 3 to 20 carbon atoms, for example $C_3$-$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl, cycloheptyl, and also to cyclopropylmethyl, cyclopropylethyl, cyclobutylmethyl, cyclobutylethyl, cyclopentylmethyl, cyclopentylethyl, cyclohexylmethyl, or $C_3$-$C_7$-cycloalkyl such as cyclopropyl, cyclobutyl, cyclopentyl, cyclohexyl, cycloheptyl, cyclopropylmethyl, cyclopropylethyl, cyclobutylmethyl, cyclopentylethyl, cyclohexylmethyl, where the bond to the rest of the molecule may be via any suitable carbon atom.

"Cycloaliphatic" radicals comprise especially the above cycloalkyl radicals and the monounsaturated analogs ("cycloalkenyl") thereof.

"Aryl" represents mono- or polycyclic, preferably mono- or bicyclic, optionally substituted aromatic radicals having 6 to 20, for example 6 to 10, ring carbon atoms, for example phenyl, biphenyl, naphthyl such as 1- or 2-naphthyl, tetrahydronaphthyl, fluorenyl, indenyl and phenanthrenyl. These aryl radicals may optionally bear 1, 2, 3, 4, 5 or 6 identical or different substituents.

"Aralkyl" represents the mono- or poly-aryl-substituted analogs of above alkyl or lower alkyl groups.

"Substituents" for radicals specified herein are especially, unless stated otherwise, selected from keto groups, —COOH, —COO-alkyl, —OH, —SH, —CN, amino, —$NO_2$, alkyl, or alkenyl groups.

"Mn" represents the number-average molecular weight and is determined in a conventional manner; more particularly, such statements relate to Mn values determined, for example, by gel permeation chromatography; especially determined by relative methods, such as gel permeation chromatography with THF as eluent and polystyrene standards, or absolute methods such as vapor phase osmometry using toluene as solvent.

"Mw" represents the weight-average molecular weight and is determined in a conventional manner; more particularly, such figures relate to Mw values determined by relative methods, such as gel permeation chromatography with THF as eluent and polystyrene standards, or absolute methods such as light scattering.

The "degree of polymerization" usually refers to the numerical mean degree of polymerization (determination method: gel permeation chromatography with THF as eluent and polystyrene standards; or GC-MS coupling).

A3) Hydrocarbyl Epoxides of the Formula (I)

Hydrocarbyl epoxides of the above formula I are compounds known per se (for example described in WO 2007/025700 or EP-A-1 422 246) or are preparable in a manner known per se (cf., for example, Sienel, G., Rieth, R. and Rowbottom, K. T. 2000. Epoxides. Ullmann's Encyclopedia of Industrial Chemistry).

Examples of suitable starting materials for epoxide preparation are in principle all compounds from the compound class of the polyalkenes, which is known per se, as described, for example, in Koch, H., Mawer, R. L. and Immel, W. 2011. Polybutenes. Ullmann's Encyclopedia of Industrial Chemistry, James L. White, Dongman Choi. 2004. Polyolefins: Processing, Structure Development, and Properties, Hanser.

More particularly, nonlimiting examples are what are called "high-reactivity" polyisobutenes which feature a high content of terminal double bonds of the above formula V. Explicit reference is made here once again to the above disclosure of high-reactivity polyisobutenes.

The preparation of useful epoxides is illustrated by way of example by the description of the preparation of a polybutene epoxide which follows.

To a solution of a polyisobutene in an apolar solvent, for example n-heptane, are added, at room temperature, formic acid and methyltrioctylammonium chloride (as described, for example, in WO 2007/025700). The reaction mixture is heated, for example to a temperature in the range from 50 to 90° C., for example about 75° C., and hydrogen peroxide solution is slowly added dropwise, while the preset temperature is maintained. The reaction mixture is subsequently stirred at the same temperature over a suitable period, for example 1 to 36 hours, for instance 10 h, and cooled to room temperature, and the phases are separated. The organic phase is washed, for example successively with aqueous $NaHSO_3$ solution, saturated $NaHCO_3$ solution and water. The organic phase is dried over $Na_2SO_4$ and the solvent is removed.

A4) Tertiary Amines of the Formula (II)

Tertiary amines of the formula (II) are likewise compounds known per se, from the group of the aliphatic or aromatic amines. Examples include:

a) Noncyclic Tertiary Amines Such as:

amines of the general formula II in which the $R_a$, $R_b$ and $R_c$ radicals are each independently $C_1$-$C_{24}$-alkyl such as methyl, ethyl, n-propyl, isopropyl, n-butyl, isobutyl, sec-butyl, tert-butyl, n-pentyl, isopentyl, n-hexyl, isohexyl, or $C_3$- to $C_{12}$-cycloalkyl such as cyclopentyl, cyclohexyl and cycloheptyl, hydroxyalkyl such as hydroxy-$C_1$-$C_{24}$-alkyl, for example the mono-hydroxy-substituted analogs of the above alkyl or cycloalkyl groups; or aralkyl, for example aryl-substituted $C_1$-$C_4$-alkyl radicals, for example benzyl. Nonlimiting examples thereof are: trimethylamine, triethylamine, tripropylamine, dimethylethylamine, methyldiethylamine, ethyldipropylamine, methyldipropylamine, dimethylpropylamine, ethyldipropylamine, diethylpropylamine, tri-(n-butyl)amine, diisopropylethylamine, tripentylamine, trihexylamine, tricyclohexylamine, ethyldicyclohexylamine, N,N-dimethylbenzylamine, N,N-dimethylcyclohexylamine, N,N-dimethylethanolamine, N,N-diethylethanolamine, N,N-dimethylethylamine, N,N-dimethylpropylamine, N,N-dimethylisopropylamine, N-ethyldiisopropylamine, tris(2-ethylhexyl)amine, N,N,N',N'-tetramethyl-1,6-hexanediamine, N,N,N',N'-tetramethyl- 1,3-propanediamine, triethanolamine, triisopropanolamine, N,N-dibutylethanolamine, N-methyldiethanolamine, N,N-dimethylisopropanolamine, N,N-di-(2-hydroxyethyl)aniline.

b) Cyclic Tertiary Amines Such as:

isopropyldimethylamine, N-methylpyrrolidone, N-methylimidazole, N-methylmorpholine, N-methylpiperidine, N-ethylpiperidine, N-ethylpyrrolidine, N-propylazepine, N-ethylmorpholine, N,N'-dimethylpiperazine.

4-aminopyridines in which the hydrogen atoms of the amino group have been replaced by $R_a$, $R_b$ or $R_c$ radicals as defined above. Examples are N,N-dimethyl-4-aminopyridine, N,N-diethyl-4-aminopyridine, 4-morpholinopyridine or 4-piperazinopyridine.

N-substituted imidazoles where the substituent is a $C_1$-$C_{24}$- or $C_1$-$C_8$-alkyl radical, for example N-methyl-, N-ethyl- or N-propylimidazole.

A5) Preparation of Inventive Quaternized Additives of the Formula (IV):

a) Quaternization

The quaternization is performed in a manner known per se.

To perform the quaternization, the tertiary amine (II) is admixed with at least one epoxide compound of the above formula (I), especially in the stoichiometric amounts required to achieve the desired quaternization.

If required, the reactants can be dissolved in a suitable organic solvent, especially alcoholic solvent, for example methanol or ethanol.

The reaction is additionally effected in the presence of stoichiometric amounts of an inorganic or especially organic acid of the above formula (III).

More particularly, organic carboxylic acids are used for this purpose, especially saturated or unsaturated, aliphatic or aromatic $C_1$-$C_{20}$ carboxylic acids, for example $C_1$-$C_4$ monocarboxylic acid, formic acid, acetic acid, propionic acid, or aromatic carboxylic acids, such as salicylic acid and benzoic acid, or fatty acids. Suitable fatty acids are straight-chain or branched, mono- or polyunsaturated, optionally substituted $C_6$-$C_{30}$-monocarboxylic acids. Examples of saturated unbranched fatty acids are caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid, behenic acid, lignoceric acid, cerotic acid and melissic acid. Examples of monounsaturated fatty acids are palmitoleic acid, oleic acid and erucic acid. Examples of diunsaturated fatty acids are sorbic acid and linoleic acid. Examples of triunsaturated fatty acids are linolenic acid and eleostearic acid. Examples of tetra- and polyunsaturated fatty acids are arachidonic acid, clupanodonic acid and docosahexaenoic acid. Examples of substituted fatty acids are ricinoleic acid ((R)-12-hydroxy-(Z)-9-octadecenoic acid). Further suitable fatty acids are naturally occurring fatty acids such as gondoic acid and nervonic acid. If double bonds are present in the fatty acids, they may be present either in cis or in trans form. The substituents are preferably selected from hydroxyl and lower alkyl groups, for example methyl and ethyl groups. In addition, keto groups or epoxy groups, as, for example, in vernolic acid, may be present in the hydrocarbyl radical. Further functional groups are cyclopropane, cyclopropene and cyclopentene rings which can be formed by bridging of two adjacent carbon atoms in the hydrocarbyl radical of the fatty acid (cf. malvalic acid and chaulmoogric acid). Particular mention should also be made of tall oil fatty acids.

Typical working temperatures here are in the range from 50 to 200° C., for example 90 to 160° C. or 100 to 140° C. The reaction time may be in the region of a few minutes or a few hours, for example about 10 minutes up to about 24 hours. The reaction can be effected at a pressure of about 1 to 20 bar, for example 1 to 10 bar, but especially in an autoclave at about standard pressure.

The reaction is additionally effected especially under inert gas, for example nitrogen.

b) Workup of the Reaction Mixture

The reaction end product thus formed can theoretically be purified further, or the solvent can be removed. Optionally, excess reagent or volatile constituents of the reaction mixture can be removed. Further purification, for example by removal of nonquaternized constituents, is not absolutely necessary, and so the reaction product may be usable as an additive merely after removal of volatile constituents, optionally after blending with further additive components (see below).

B) Further Additive Components

The fuel additized with the inventive quaternized additive is a gasoline fuel or especially a middle distillate fuel, in particular a diesel fuel.

The fuel may comprise further customary additives to improve efficacy and/or suppress wear.

In the case of diesel fuels, these are primarily customary detergent additives, carrier oils, cold flow improvers, lubricity improvers, corrosion inhibitors, demulsifiers, dehazers, antifoams, cetane number improvers, combustion improvers, antioxidants or stabilizers, antistats, metallocenes, metal deactivators, dyes and/or solvents.

In the case of gasoline fuels, these are in particular lubricity improvers (friction modifiers), corrosion inhibitors, demulsifiers, dehazers, antifoams, combustion improvers, antioxidants or stabilizers, antistats, metallocenes, metal deactivators, dyes and/or solvents.

Typical examples of suitable coadditives are listed in the following section:

B1) Detergent Additives

The customary detergent additives are preferably amphiphilic substances which possess at least one hydrophobic hydrocarbyl radical with a number-average molecular weight ($M_n$) of 85 to 20 000 and at least one polar moiety selected from:

(Da) mono- or polyamino groups having up to 6 nitrogen atoms, at least one nitrogen atom having basic properties;

(Db) nitro groups, optionally in combination with hydroxyl groups;

(Dc) hydroxyl groups in combination with mono- or polyamino groups, at least one nitrogen atom having basic properties;

(Dd) carboxyl groups or the alkali metal or alkaline earth metal salts thereof;

(De) sulfonic acid groups or the alkali metal or alkaline earth metal salts thereof;

(Df) polyoxy-$C_2$- to $C_4$-alkylene moieties terminated by hydroxyl groups, mono- or polyamino groups, at least one nitrogen atom having basic properties, or by carbamate groups;

(Dg) carboxylic ester groups;

(Dh) moieties derived from succinic anhydride and having hydroxyl and/or amino and/or amido and/or imido groups; and/or (Di) moieties obtained by Mannich reaction of substituted phenols with aldehydes and mono- or polyamines.

The hydrophobic hydrocarbon radical in the above detergent additives, which ensures the adequate solubility in the fuel, has a number-average molecular weight ($M_n$) of 85 to 20 000, preferably of 113 to 10 000, more preferably of 300 to 5000, even more preferably of 300 to 3000, even more especially preferably of 500 to 2500 and especially of 700 to 2500, in particular of 800 to 1500. Useful typical hydrophobic hydrocarbyl radicals are especially polypropenyl, polybutenyl and polyisobutenyl radicals with a number-average molecular weight $M_n$ of preferably in each case 300 to 5000, more preferably 300 to 3000, even more preferably 500 to 2500, even more especially preferably 700 to 2500 and especially 800 to 1500 into consideration.

Examples of the above groups of detergent additives include the following:

Additives comprising mono- or polyamino groups (Da) are preferably polyalkenemono- or polyalkenepolyamines based on polypropene or on high-reactivity (i.e. having predominantly terminal double bonds) or conventional (i.e. having predominantly internal double bonds) polybutene or polyisobutene having $M_n$=300 to 5000, more preferably 500 to 2500 and especially 700 to 2500. Such additives based on high-reactivity polyisobutene, which can be prepared from the polyisobutene which may comprise up to 20% by weight of n-butene units by hydroformylation and reductive amination with ammonia, monoamines or polyamines such as dimethylaminopropylamine, ethylenediamine, diethylenetriamine, triethylenetetramine or tetraethylenepentamine, are known especially from EP-A 244 616. When polybutene or polyisobutene having predominantly internal double bonds (usually in the β and γ positions) are used as starting materials in the preparation of the additives, a possible preparative route is by chlorination and subsequent amination or by oxidation of the double bond with air or ozone to give the carbonyl or carboxyl compound and subsequent amination under reductive (hydrogenating) conditions. The amines used here for the amination may be, for example, ammonia, monoamines or the abovementioned polyamines. Corresponding additives based on polypropene are described more particularly in WO-A 94/24231.

Further particular additives comprising monoamino groups (Da) are the hydrogenation products of the reaction products of polyisobutenes having an average degree of polymerization P=5 to 100 with nitrogen oxides or mixtures of nitrogen oxides and oxygen, as described more particularly in WO-A 97/03946.

Further particular additives comprising monoamino groups (Da) are the compounds obtainable from polyisobutene epoxides by reaction with amines and subsequent dehydration and reduction of the amino alcohols, as described more particularly in DE-A 196 20 262.

Additives comprising nitro groups (Db), optionally in combination with hydroxyl groups, are preferably reaction products of polyisobutenes having an average degree of polymerization P=5 to 100 or 10 to 100 with nitrogen oxides or mixtures of nitrogen oxides and oxygen, as described more particularly in WO-A 96/03367 and in WO-A 96/03479. These reaction products are generally mixtures of pure nitropolyisobutenes (e.g. α,β-dinitropolyisobutene) and mixed hydroxynitropolyisobutenes (e.g. α-nitro-β-hydroxypolyisobutene).

Additives comprising hydroxyl groups in combination with mono- or polyamino groups (Dc) are especially reaction products of polyisobutene epoxides obtainable from polyisobutene having preferably predominantly terminal double bonds and $M_n$=300 to 5000, with ammonia or mono- or polyamines, as described more particularly in EP-A 476 485.

Additives comprising carboxyl groups or their alkali metal or alkaline earth metal salts (Dd) are preferably copolymers of $C_2$- to $C_{40}$-olefins with maleic anhydride which have a total molar mass of 500 to 20 000 and some or all of whose carboxyl groups have been converted to the alkali metal or alkaline earth metal salts and any remainder of the carboxyl groups has been reacted with alcohols or amines. Such additives are disclosed more particularly by EP-A 307 815. Such additives serve mainly to prevent valve seat wear and can, as described in WO-A 87/01126, advantageously be used in combination with customary fuel detergents such as poly(iso)buteneamines or polyetheramines.

Additives comprising sulfonic acid groups or their alkali metal or alkaline earth metal salts (De) are preferably alkali metal or alkaline earth metal salts of an alkyl sulfosuccinate, as described more particularly in EP-A 639 632. Such additives serve mainly to prevent valve seat wear and can be used advantageously in combination with customary fuel detergents such as poly(iso)buteneamines or polyetheramines.

Additives comprising polyoxy-$C_2$-$C_4$-alkylene moieties (Df) are preferably polyethers or polyetheramines which are obtainable by reaction of $C_2$- to $C_{60}$-alkanols, $C_6$- to $C_{30}$-alkanediols, mono- or di-$C_2$- to $C_{30}$-alkylamines, $C_1$- to $C_{30}$-alkylcyclohexanols or $C_1$- to $C_{30}$-alkylphenols with 1 to 30 mol of ethylene oxide and/or propylene oxide and/or butylene oxide per hydroxyl group or amino group and, in the case of the polyetheramines, by subsequent reductive amination with ammonia, monoamines or polyamines. Such products are described more particularly in EP-A 310 875, EP-A 356 725, EP-A 700 985 and U.S. Pat. No. 4,877,416. In the case of polyethers, such products also have carrier oil properties. Typical examples thereof are tridecanol butoxylates or isotridecanol butoxylates, isononylphenol butoxylates and also polyisobutenol butoxylates and propoxylates, and also the corresponding reaction products with ammonia.

Additives comprising carboxylic ester groups (Dg) are preferably esters of mono-, di- or tricarboxylic acids with long-chain alkanols or polyols, especially those having a minimum viscosity of 2 mm$^2$/s at 100° C., as described more particularly in DE-A 38 38 918. The mono-, di- or tricarboxylic acids used may be aliphatic or aromatic acids, and particularly suitable ester alcohols or ester polyols are long-chain representatives having, for example, 6 to 24 carbon atoms. Typical representatives of the esters are adipates, phthalates, isophthalates, terephthalates and trimellitates of isooctanol, of isononanol, of isodecanol and of isotridecanol. Such products also satisfy carrier oil properties.

Additives comprising moieties derived from succinic anhydride and having hydroxyl and/or amino and/or amido and/or especially imido groups (Dh) are preferably corresponding derivatives of alkyl- or alkenyl-substituted succinic anhydride and especially the corresponding derivatives of polyisobutenylsuccinic anhydride which are obtainable by reacting conventional or high-reactivity polyisobutene having $M_n$=preferably 300 to 5000, more preferably 300 to 3000, even more preferably 500 to 2500, even more especially preferably 700 to 2500 and especially 800 to 1500, with maleic anhydride by a thermal route in an ene reaction or via the chlorinated polyisobutene. The moieties having hydroxyl and/or amino and/or amido and/or imido groups are, for example, carboxylic acid groups, acid amides of monoamines, acid amides of di- or polyamines which, in addition to the amide function, also have free amine groups, succinic acid derivatives having an acid and an amide function, carboximides with monoamines, carboximides with di- or polyamines which, in addition to the imide function, also have free amine groups, or diimides which are formed by the reaction of di- or polyamines with two succinic acid derivatives. In the presence of imido moieties D(h), the further detergent additive in the context of the present invention is, however, used only up to a maximum of 100% of the weight of compounds with betaine structure. Such fuel additives are common knowledge and are described, for example, in documents (1) and (2). They are preferably the reaction products of alkyl- or alkenyl-substituted succinic acids or derivatives thereof with amines and more preferably the reaction products of polyisobutenyl-substituted succinic acids or derivatives thereof with amines. Of particular interest in this context are reaction products with aliphatic polyamines (polyalkyleneimines) such as especially ethylenediamine, diethylenetriamine, triethylenetetramine, tetraethylenepentamine, pentaethylenehexamine and hexaethyleneheptamine, which have an imide structure.

Additives comprising moieties (Di) obtained by Mannich reaction of substituted phenols with aldehydes and mono- or polyamines are preferably reaction products of polyisobutene-substituted phenols with formaldehyde and mono- or polyamines such as ethylenediamine, diethylenetriamine, triethylenetetramine, tetraethylenepentamine or dimethylaminopropylamine. The polyisobutenyl-substituted phenols may originate from conventional or high-reactivity polyisobutene having $M_n$=300 to 5000. Such "polyisobutene Mannich bases" are described more particularly in EP-A 831 141.

One or more of the detergent additives mentioned can be added to the fuel in such an amount that the dosage of these detergent additives is preferably 25 to 2500 ppm by weight, especially 75 to 1500 ppm by weight, in particular 150 to 1000 ppm by weight.

B2) Carrier Oils

Carrier oils additionally used may be of mineral or synthetic nature. Suitable mineral carrier oils are fractions obtained in crude oil processing, such as brightstock or base oils having viscosities, for example, from the SN 500-2000 class; but also aromatic hydrocarbons, paraffinic hydrocarbons and alkoxyalkanols. Likewise useful is a fraction which is obtained in the refining of mineral oil and is known as "hydrocrack oil" (vacuum distillate cut having a boiling range of from about 360 to 500° C., obtainable from natural mineral oil which has been catalytically hydrogenated under high pressure and isomerized and also deparaffinized). Likewise suitable are mixtures of the abovementioned mineral carrier oils.

Examples of suitable synthetic carrier oils are polyolefins (polyalphaolefins or polyinternalolefins), (poly)esters, (poly)alkoxylates, polyethers, aliphatic polyetheramines, alkylphenol-started polyethers, alkylphenol-started polyetheramines and carboxylic esters of long-chain alkanols.

Examples of suitable polyolefins are olefin polymers having $M_n$=400 to 1800, in particular based on polybutene or polyisobutene (hydrogenated or unhydrogenated).

Examples of suitable polyethers or polyetheramines are preferably compounds comprising polyoxy-$C_2$- to $C_a$-alkylene moieties which are obtainable by reacting $C_2$- to $C_{60}$-alkanols, $C_6$- to $C_{30}$-alkanediols, mono- or di-$C_2$- to $C_{30}$-alkylamines, $C_1$- to $C_{30}$-alkylcyclohexanols or $C_1$- to $C_{30}$-alkylphenols with 1 to 30 mol of ethylene oxide and/or propylene oxide and/or butylene oxide per hydroxyl group or amino group, and, in the case of the polyetheramines, by subsequent reductive amination with ammonia, monoamines or polyamines. Such products are described more particularly in EP-A 310 875, EP-A 356 725, EP-A 700 985 and U.S. Pat. No. 4,877,416. For example, the polyetheramines used may be poly-$C_2$- to $C_6$-alkylene oxide amines or functional derivatives thereof. Typical examples thereof are tridecanol butoxylates or isotridecanol butoxylates, isononylphenol butoxylates and also polyisobutenol butoxylates and propoxylates, and also the corresponding reaction products with ammonia.

Examples of carboxylic esters of long-chain alkanols are more particularly esters of mono-, di- or tricarboxylic acids with long-chain alkanols or polyols, as described more particularly in DE-A 38 38 918. The mono-, di- or tricarboxylic acids used may be aliphatic or aromatic acids; particularly suitable ester alcohols or ester polyols are long-chain representatives having, for example, 6 to 24 carbon atoms. Typical representatives of the esters are adipates, phthalates, isophthalates, terephthalates and trimellitates of isooctanol, isononanol, isodecanol and isotridecanol, for example di(n- or isotridecyl) phthalate.

Further suitable carrier oil systems are described, for example, in DE-A 38 26 608, DE-A 41 42 241, DE-A 43 09 074, EP-A 452 328 and EP-A 548 617.

Examples of particularly suitable synthetic carrier oils are alcohol-started polyethers having about 5 to 35, preferably about 5 to 30, more preferably 10 to 30 and especially 15 to 30 $C_3$- to $C_6$-alkylene oxide units, for example propylene oxide, n-butylene oxide and isobutylene oxide units, or mixtures thereof, per alcohol molecule. Nonlimiting examples of suitable starter alcohols are long-chain alkanols or phenols substituted by long-chain alkyl in which the long-chain alkyl radical is especially a straight-chain or branched $C_6$- to $C_{18}$-alkyl radical. Particular examples include tridecanol and nonylphenol. Particularly preferred alcohol-started polyethers are the reaction products (polyetherification products) of monohydric aliphatic $C_6$- to $C_{18}$-alcohols with $C_3$- to $C_6$-alkylene oxides. Examples of monohydric aliphatic $C_6$-$C_{18}$-alcohols are hexanol, heptanol, octanol, 2-ethylhexanol, nonyl alcohol, decanol, 3-propylheptanol, undecanol, dodecanol, tridecanol, tetradecanol, pentadecanol, hexadecanol, octadecanol and the constitutional and positional isomers thereof. The alcohols can be used either in the form of the pure isomers or in the form of technical grade mixtures. A particularly preferred alcohol is tridecanol. Examples of $C_3$- to $C_6$-alkylene oxides are propylene oxide, such as 1,2-propylene oxide, butylene oxide, such as 1,2-butylene oxide, 2,3-butylene oxide, isobutylene oxide or tetrahydrofuran, pentylene oxide and hexylene oxide. Particular preference among these is given to $C_3$- to $C_4$-alkylene oxides, i.e. propylene oxide such as 1,2-propylene oxide and butylene oxide such as 1,2-butylene oxide, 2,3-butylene oxide and isobutylene oxide. Especially butylene oxide is used.

Further suitable synthetic carrier oils are alkoxylated alkylphenols, as described in DE-A 10 102 913.

Particular carrier oils are synthetic carrier oils, particular preference being given to the above-described alcohol-started polyethers.

The carrier oil or the mixture of different carrier oils is added to the fuel in an amount of preferably 1 to 1000 ppm by weight, more preferably of 10 to 500 ppm by weight and especially of 20 to 100 ppm by weight.

B3) Cold Flow Improvers

Suitable cold flow improvers are in principle all organic compounds which are capable of improving the flow performance of middle distillate fuels or diesel fuels under cold conditions. For the intended purpose, they must have sufficient oil solubility. More particularly, useful cold flow improvers for this purpose are the cold flow improvers (middle distillate flow improvers, MDFIs) typically used in the case of middle distillates of fossil origin, i.e. in the case of customary mineral diesel fuels. However, it is also possible to use organic compounds which partly or predominantly have the properties of a wax antisettling additive (WASA) when used in customary diesel fuels. They can also act partly or predominantly as nucleators. It is also possible to use mixtures of organic compounds effective as MDFIs and/or effective as WASAs and/or effective as nucleators.

The cold flow improver is typically selected from:
(K1) copolymers of a $C_2$- to $C_{40}$-olefin with at least one further ethylenically unsaturated monomer;
(K2) comb polymers;
(K3) polyoxyalkylenes;
(K4) polar nitrogen compounds;
(K5) sulfocarboxylic acids or sulfonic acids or derivatives thereof; and
(K6) poly(meth)acrylic esters.

It is possible to use either mixtures of different representatives from one of the particular classes (K1) to (K6) or mixtures of representatives from different classes (K1) to (K6).

Suitable $C_2$- to $C_{40}$-olefin monomers for the copolymers of class (K1) are, for example, those having 2 to 20 and especially 2 to 10 carbon atoms, and 1 to 3 and preferably 1 or 2 carbon-carbon double bonds, especially having one carbon-carbon double bond. In the latter case, the carbon-carbon double bond may be arranged either terminally (α-olefins) or internally. However, preference is given to α-olefins, particular preference to α-olefins having 2 to 6 carbon atoms, for example propene, 1-butene, 1-pentene, 1-hexene and in particular ethylene.

In the copolymers of class (K1), the at least one further ethylenically unsaturated monomer is preferably selected from alkenyl carboxylates, (meth)acrylic esters and further olefins.

When further olefins are also copolymerized, they are preferably higher in molecular weight than the abovementioned $C_2$- to $C_{40}$-olefin base monomer. When, for example, the olefin base monomer used is ethylene or propene, suitable further olefins are especially $C_{10}$- to $C_{40}$-α-olefins. Further olefins are in most cases only additionally copolymerized when monomers with carboxylic ester functions are also used.

Suitable (meth)acrylic esters are, for example, esters of (meth)acrylic acid with $C_1$- to $C_{20}$-alkanols, especially $C_1$- to $C_{10}$-alkanols, in particular with methanol, ethanol, propanol, isopropanol, n-butanol, sec-butanol, isobutanol, tert-butanol, pentanol, hexanol, heptanol, octanol, 2-ethylhexanol, nonanol and decanol, and structural isomers thereof.

Suitable alkenyl carboxylates are, for example, $C_2$- to $C_{14}$-alkenyl esters, for example the vinyl and propenyl esters, of carboxylic acids having 2 to 21 carbon atoms, whose hydrocarbyl radical may be linear or branched. Among these, preference is given to the vinyl esters. Among the carboxylic acids with a branched hydrocarbyl radical, preference is given to those whose branch is in the α position to the carboxyl group, and the α-carbon atom is more preferably tertiary, i.e. the carboxylic acid is what is called a neocarboxylic acid. However, the hydrocarbyl radical of the carboxylic acid is preferably linear.

Examples of suitable alkenyl carboxylates are vinyl acetate, vinyl propionate, vinyl butyrate, vinyl 2-ethylhexanoate, vinyl neopentanoate, vinyl hexanoate, vinyl neononanoate, vinyl neodecanoate and the corresponding propenyl esters, preference being given to the vinyl esters. A particularly preferred alkenyl carboxylate is vinyl acetate; typical copolymers of group (K1) resulting therefrom are ethylene-vinyl acetate copolymers ("EVAs"), which are some of the most frequently used.

Ethylene-vinyl acetate copolymers usable particularly advantageously and the preparation thereof are described in WO 99/29748.

Suitable copolymers of class (K1) are also those which comprise two or more different alkenyl carboxylates in copolymerized form, which differ in the alkenyl function and/or in the carboxylic acid group. Likewise suitable are copolymers which, as well as the alkenyl carboxylate(s), comprise at least one olefin and/or at least one (meth)acrylic ester in copolymerized form.

Terpolymers of a $C_2$- to $C_{40}$-α-olefin, a $C_1$- to $C_{20}$-alkyl ester of an ethylenically unsaturated monocarboxylic acid having 2 to 15 carbon atoms and a $C_2$- to $C_{14}$-alkenyl ester of a saturated monocarboxylic acid having 2 to 21 carbon atoms are also suitable as copolymers of class (K1). Terpolymers of this kind are described in WO 2005/054314. A typical terpolymer of this kind is formed from ethylene, 2-ethylhexyl acrylate and vinyl acetate.

The at least one or the further ethylenically unsaturated monomer(s) are copolymerized in the copolymers of class (K1) in an amount of preferably 1 to 50% by weight, especially 10 to 45% by weight and in particular 20 to 40% by weight, based on the overall copolymer. The main proportion in terms of weight of the monomer units in the copolymers of class (K1) therefore originates generally from the $C_2$ to $C_{40}$ base olefins.

The copolymers of class (K1) preferably have a number-average molecular weight $M_n$ of 1000 to 20 000, more preferably of 1000 to 10 000 and especially of 1000 to 8000.

Typical comb polymers of component (K2) are, for example, obtainable by the copolymerization of maleic anhydride or fumaric acid with another ethylenically unsaturated monomer, for example with an α-olefin or an unsaturated ester, such as vinyl acetate, and subsequent esterification of the anhydride or acid function with an alcohol having at least 10 carbon atoms. Further suitable comb polymers are copolymers of α-olefins and esterified comonomers, for example esterified copolymers of styrene and maleic anhydride or esterified copolymers of styrene and fumaric acid. Suitable comb polymers may also be polyfumarates or polymaleates. Homo- and copolymers of vinyl ethers are also suitable comb polymers. Comb polymers suitable as components of class (K2) are, for example, also those described in WO 2004/035715 and in "Comb-Like Polymers. Structure and Properties", N. A. Plate and V. P. Shibaev, J. Poly. Sci. Macromolecular Revs. 8, pages 117 to 253 (1974). Mixtures of comb polymers are also suitable.

Polyoxyalkylenes suitable as components of class (K3) are, for example, polyoxyalkylene esters, polyoxyalkylene ethers, mixed polyoxyalkylene ester/ethers and mixtures thereof. These polyoxyalkylene compounds preferably comprise at least one linear alkyl group, preferably at least two linear alkyl groups, each having 10 to 30 carbon atoms and a polyoxyalkylene group having a number-average molecular weight of up to 5000. Such polyoxyalkylene compounds are described, for example, in EP-A 061 895 and also in U.S.

Pat. No. 4,491,455. Particular polyoxyalkylene compounds are based on polyethylene glycols and polypropylene glycols having a number-average molecular weight of 100 to 5000. Additionally suitable are polyoxyalkylene mono- and diesters of fatty acids having 10 to 30 carbon atoms, such as stearic acid or behenic acid.

Polar nitrogen compounds suitable as components of class (K4) may be either ionic or nonionic and preferably have at least one substituent, especially at least two substituents, in the form of a tertiary nitrogen atom of the general formula >$NR^7$ in which $R^1$ is a $C_8$- to $C_{40}$-hydrocarbyl radical. The nitrogen substituents may also be quaternized, i.e. be in cationic form. An example of such nitrogen compounds is that of ammonium salts and/or amides which are obtainable by the reaction of at least one amine substituted by at least one hydrocarbyl radical with a carboxylic acid having 1 to 4 carboxyl groups or with a suitable derivative thereof. The amines preferably comprise at least one linear $C_8$- to $C_{40}$-alkyl radical. Primary amines suitable for preparing the polar nitrogen compounds mentioned are, for example, octylamine, nonylamine, decylamine, undecylamine, dodecylamine, tetradecylamine and the higher linear homologs; secondary amines suitable for this purpose are, for example, dioctadecylamine and methylbehenylamine. Also suitable for this purpose are amine mixtures, especially amine mixtures obtainable on the industrial scale, such as fatty amines or hydrogenated tallamines, as described, for example, in Ullmann's Encyclopedia of Industrial Chemistry, 6th Edition, "Amines, aliphatic" chapter. Acids suitable for the reaction are, for example, cyclohexane-1,2-dicarboxylic acid, cyclohexene-1,2-dicarboxylic acid, cyclopentane-1,2-dicarboxylic acid, naphthalenedicarboxylic acid, phthalic acid, isophthalic acid, terephthalic acid, and succinic acids substituted by long-chain hydrocarbyl radicals.

More particularly, the component of class (K4) is an oil-soluble reaction product of poly($C_2$- to $C_{20}$-carboxylic acids) having at least one tertiary amino group with primary or secondary amines. The poly($C_2$- to $C_{20}$-carboxylic acids) which have at least one tertiary amino group and form the basis of this reaction product comprise preferably at least 3 carboxyl groups, especially 3 to 12 and in particular 3 to 5 carboxyl groups. The carboxylic acid units in the polycarboxylic acids have preferably 2 to 10 carbon atoms, and are especially acetic acid units. The carboxylic acid units are suitably bonded to the polycarboxylic acids, usually via one or more carbon and/or nitrogen atoms. They are preferably attached to tertiary nitrogen atoms which, in the case of a plurality of nitrogen atoms, are bonded via hydrocarbon chains.

The component of class (K4) is preferably an oil-soluble reaction product based on poly($C_2$- to $C_{20}$-carboxylic acids) which have at least one tertiary amino group and are of the general formula IIa or IIb

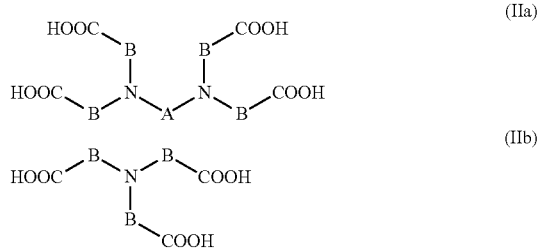

in which the variable A denotes a straight-chain or branched $C_2$- to $C_6$-alkylene group or the moiety of the formula III

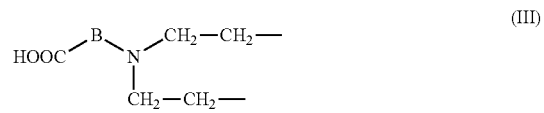

and the variable B denotes a $C_1$- to $C_{19}$-alkylene group. The compounds of the general formulae IIa and IIb especially have the properties of a WASA.

Moreover, the preferred oil-soluble reaction product of component (K4), especially that of the general formula IIa or IIb, is an amide, an amide-ammonium salt or an ammonium salt in which no, one or more carboxylic acid groups have been converted to amide groups.

Straight-chain or branched $C_2$- to $C_6$-alkylene groups of the variable A are, for example, 1,1-ethylene, 1,2-propylene, 1,3-propylene, 1,2-butylene, 1,3-butylene, 1,4-butylene, 2-methyl-1,3-propylene, 1,5-pentylene, 2-methyl-1,4-butylene, 2,2-dimethyl-1,3-propylene, 1,6-hexylene (hexamethylene) and especially 1,2-ethylene. The variable A comprises preferably 2 to 4 and especially 2 or 3 carbon atoms.

$C_1$- to $C_{19}$-alkylene groups of the variable B are, for example, 1,2-ethylene, 1,3-propylene, 1,4-butylene, hexamethylene, octamethylene, decamethylene, dodecamethylene, tetradecamethylene, hexadecamethylene, octadecamethylene, nonadecamethylene and especially methylene. The variable B comprises preferably 1 to 10 and especially 1 to 4 carbon atoms.

The primary and secondary amines as a reaction partner for the polycarboxylic acids to form component (K4) are typically monoamines, especially aliphatic monoamines. These primary and secondary amines may be selected from a multitude of amines which bear hydrocarbyl radicals which may optionally be bonded to one another.

These parent amines of the oil-soluble reaction products of component (K4) are usually secondary amines and have the general formula $HN(R^8)_2$ in which the two variables $R^8$ are each independently straight-chain or branched $C_{10}$- to $C_{30}$-alkyl radicals, especially $C_{14}$- to $C_{24}$-alkyl radicals. These relatively long-chain alkyl radicals are preferably straight-chain or only slightly branched. In general, the secondary amines mentioned, with regard to their relatively long-chain alkyl radicals, derive from naturally occurring fatty acids and from derivatives thereof. The two $R^8$ radicals are preferably the same.

The secondary amines mentioned may be bonded to the polycarboxylic acids by means of amide structures or in the form of the ammonium salts; it is also possible for only a portion to be present as amide structures and another portion as ammonium salts. Preferably only few, if any, free acid groups are present. The oil-soluble reaction products of component (K4) are preferably present completely in the form of the amide structures.

Typical examples of such components (K4) are reaction products of nitrilotriacetic acid, of ethylenediaminetetraacetic acid or of propylene-1,2-diaminetetraacetic acid with in each case 0.5 to 1.5 mol per carboxyl group, especially 0.8 to 1.2 mol per carboxyl group, of dioleylamine, dipalmitamine, dicocoamine, distearylamine, dibehenylamine or especially ditallamine. A particularly preferred component (K4) is the reaction product of 1 mol of ethylenediaminetetraacetic acid and 4 mol of hydrogenated ditallamine.

Further typical examples of component (K4) include the N,N-dialkylammonium salts of 2-N',N'-dialkylamidobenzoates, for example the reaction product of 1 mol of phthalic anhydride and 2 mol of ditallamine, the latter being hydrogenated or unhydrogenated, and the reaction product of 1 mol of an alkenylspirobislactone with 2 mol of a dialkylamine, for example ditallamine and/or tallamine, the latter two being hydrogenated or unhydrogenated.

Further typical structure types for the component of class (K4) are cyclic compounds with tertiary amino groups or condensates of long-chain primary or secondary amines with carboxylic acid-containing polymers, as described in WO 93/18115.

Sulfocarboxylic acids, sulfonic acids or derivatives thereof which are suitable as cold flow improvers of the component of class (K5) are, for example, the oil-soluble carboxamides and carboxylic esters of ortho-sulfobenzoic acid, in which the sulfonic acid function is present as a sulfonate with alkyl-substituted ammonium cations, as described in EP-A 261 957.

Poly(meth)acrylic esters suitable as cold flow improvers of the component of class (K6) are either homo- or copolymers of acrylic and methacrylic esters. Preference is given to copolymers of at least two different (meth)acrylic esters which differ with regard to the esterified alcohol. The copolymer optionally comprises another different olefinically unsaturated monomer in copolymerized form. The weight-average molecular weight of the polymer is preferably 50 000 to 500 000. A particularly preferred polymer is a copolymer of methacrylic acid and methacrylic esters of saturated $C_{14}$- and $C_{15}$-alcohols, the acid groups having been neutralized with hydrogenated tallamine. Suitable poly(meth)acrylic esters are described, for example, in WO 00/44857.

The cold flow improver or the mixture of different cold flow improvers is added to the middle distillate fuel or diesel fuel in a total amount of preferably 10 to 5000 ppm by weight, more preferably of 20 to 2000 ppm by weight, even more preferably of 50 to 1000 ppm by weight and especially of 100 to 700 ppm by weight, for example of 200 to 500 ppm by weight.

B4) Lubricity Improvers

Suitable lubricity improvers or friction modifiers are based typically on fatty acids or fatty acid esters. Typical examples are tall oil fatty acid, as described, for example, in WO 98/004656, and glyceryl monooleate. The reaction products, described in U.S. Pat. No. 6,743,266 B2, of natural or synthetic oils, for example triglycerides, and alkanolamines are also suitable as such lubricity improvers.

B5) Corrosion Inhibitors

Suitable corrosion inhibitors are, for example, succinic esters, in particular with polyols, fatty acid derivatives, for example oleic esters, oligomerized fatty acids, substituted ethanolamines, and products sold under the trade name RC 4801 (Rhein Chemie Mannheim, Germany) or HiTEC 536 (Ethyl Corporation).

B6) Demulsifiers

Suitable demulsifiers are, for example, the alkali metal or alkaline earth metal salts of alkyl-substituted phenol- and naphthalenesulfonates and the alkali metal or alkaline earth metal salts of fatty acids, and also neutral compounds such as alcohol alkoxylates, e.g. alcohol ethoxylates, phenol alkoxylates, e.g. tert-butylphenol ethoxylate or tert-pentylphenol ethoxylate, fatty acids, alkylphenols, condensation products of ethylene oxide (EO) and propylene oxide (PO), for example including in the form of EO/PO block copolymers, polyethyleneimines or else polysiloxanes.

B7) Dehazers

Suitable dehazers are, for example, alkoxylated phenol-formaldehyde condensates, for example the products available under the trade names NALCO 7D07 (Nalco) and TOLAD 2683 (Petrolite).

B8) Antifoams

Suitable antifoams are, for example, polyether-modified polysiloxanes, for example the products available under the trade names TEGOPREN 5851 (Goldschmidt), Q 25907 (Dow Corning) and RHODOSIL (Rhone Poulenc).

B9) Cetane Number Improvers

Suitable cetane number improvers are, for example, aliphatic nitrates such as 2-ethylhexyl nitrate and cyclohexyl nitrate and peroxides such as di-tert-butyl peroxide.

B10) Antioxidants

Suitable antioxidants are, for example, substituted phenols, such as 2,6-di-tert-butylphenol and 6-di-tert-butyl-3-methylphenol, and also phenylenediamines such as N,N'-di-sec-butyl-p-phenylenediamine.

B11) Metal Deactivators

Suitable metal deactivators are, for example, salicylic acid derivatives such as N,N'-disalicylidene-1,2-propanediamine.

B12) Solvents

Suitable solvents are, for example, nonpolar organic solvents such as aromatic and aliphatic hydrocarbons, for example toluene, xylenes, white spirit and products sold under the trade names SHELLSOL (Royal Dutch/Shell Group) and EXXSOL (ExxonMobil), and also polar organic solvents, for example, alcohols such as 2-ethylhexanol, decanol and isotridecanol. Such solvents are usually added to the diesel fuel together with the aforementioned additives and coadditives, which they are intended to dissolve or dilute for better handling.

C) Fuels

The inventive additive is outstandingly suitable as a fuel additive and can be used in principle in any fuels. It brings about a whole series of advantageous effects in the operation of internal combustion engines with fuels. Preference is given to using the inventive quaternized additive in middle distillate fuels, especially diesel fuels.

The present invention therefore also provides fuels, especially middle distillate fuels, with a content of the inventive quaternized additive which is effective as an additive for achieving advantageous effects in the operation of internal combustion engines, for example of diesel engines, especially of direct injection diesel engines, in particular of diesel engines with common rail injection systems. This effective content (dosage) in inventive fuels is generally 10 to 5000 ppm by weight, preferably 20 to 1500 ppm by weight, especially 25 to 1000 ppm by weight, in particular 30 to 750 ppm by weight, based in each case on the total amount of fuel.

Middle distillate fuels such as diesel fuels or heating oils are preferably mineral oil raffinates which typically have a boiling range from 100 to 400° C. These are usually distillates having a 95% point up to 360° C. or even higher. These may also be what is called "ultra low sulfur diesel" or "city diesel", characterized by a 95% point of, for example, not more than 345° C. and a sulfur content of not more than 0.005% by weight or by a 95% point of, for example, 285° C. and a sulfur content of not more than 0.001% by weight. In addition to the mineral middle distillate fuels or diesel fuels obtainable by refining, those obtainable by coal gasification or gas liquefaction ["gas to liquid" (GTL) fuels] or by biomass liquefaction ["biomass to liquid" (BTL) fuels] are also suitable. Also suitable are mixtures of the aforementioned middle distillate fuels or diesel fuels with renewable fuels, such as biodiesel or bioethanol.

The qualities of the heating oils and diesel fuels are laid down in detail, for example, in DIN 51603 and EN 590 (cf. also Ullmann's Encyclopedia of Industrial Chemistry, 5th edition, Volume A12, p. 617 ff.).

In addition to the use thereof in the abovementioned middle distillate fuels of fossil, vegetable or animal origin, which are essentially hydrocarbon mixtures, the inventive quaternized additive can also be used in mixtures of such middle distillates with biofuel oils (biodiesel). Such mixtures are also encompassed by the term "middle distillate fuel" in the context of the present invention. They are commercially available and usually comprise the biofuel oils in minor amounts, typically in amounts of 1 to 30% by weight, especially of 3 to 10% by weight, based on the total amount of middle distillate of fossil, vegetable or animal origin and biofuel oil.

Biofuel oils are generally based on fatty acid esters, preferably essentially on alkyl esters of fatty acids which derive from vegetable and/or animal oils and/or fats. Alkyl esters are typically understood to mean lower alkyl esters, especially $C_1$-$C_4$-alkyl esters, which are obtainable by transesterifying the glycerides which occur in vegetable and/or animal oils and/or fats, especially triglycerides, by means of lower alcohols, for example ethanol or in particular methanol ("FAME"). Typical lower alkyl esters based on vegetable and/or animal oils and/or fats, which find use as a biofuel oil or components thereof, are, for example, sunflower methyl ester, palm oil methyl ester ("PME"), soya oil methyl ester ("SME") and especially rapeseed oil methyl ester ("RME").

The middle distillate fuels or diesel fuels are more preferably those having a low sulfur content, i.e. having a sulfur content of less than 0.05% by weight, preferably of less than 0.02% by weight, more particularly of less than 0.005% by weight and especially of less than 0.001% by weight of sulfur.

Useful gasoline fuels include all commercial gasoline fuel compositions. One typical representative which shall be mentioned here is the Eurosuper base fuel to EN 228, which is customary on the market. In addition, gasoline fuel compositions of the specification according to WO 00/47698 are also possible fields of use for the present invention.

The inventive quaternized additive is especially suitable as a fuel additive in fuel compositions, especially in diesel fuels, for overcoming the problems outlined at the outset in direct injection diesel engines, in particular in those with common rail injection systems.

The invention is now illustrated in detail by the working examples which follow:

Experimental:
Reagents Used:
Polyisobutene 1000: Glissopal® 1000 from BASF, Mn=1000
Formic acid from BASF, CAS 64-18-6
Methyltrioctylammonium chloride from Aldrich, 63393-96-4
n-Heptane from Aldrich, CAS 142-82-5
Methanol from Aldrich, CAS 67-56-1
Acetic acid (99-100%) from Roth, CAS 64-19-7
N-Methylpyrrolidine from BASF, CAS 120-94-5
1-Dodecene oxide from Aldrich, CAS 2855-19-8
1-Tetradecene oxide, CAS 3234-28-4
1-Hexadecene oxide, CAS 7320-37-8
Isopropanol from Aldrich, CAS 67-63-0
Trimethylamine NMe$_3$ (>99.5% (w/w)) from BASF, CAS 75-50-3
Tall oil fatty acid: Kerokorr® LA 99 C from BASF, TAN 199 mg KOH/g
N,N-Dimethylethanolamine from BASF, CAS 108-01-0
Salicylic acid from Merck, CAS 69-72-7

A. General Test Methods

These methods form part of the general disclosure and are not limited to the compounds specifically tested.

Engine Test

1. XUD9 test—determination of flow restriction

The procedure is according to the standard provisions of CEC F-23-1-01.

2. DW10 test—determination of power loss as a result of injector deposits in the common rail diesel engine 2.1. DW10-KC—keep-clean test The keep-clean test is based on CEC test procedure F-098-08 Issue 5. This is done using the same test setup and engine type (PEUGEOT DW10) as in the CEC procedure.

Change and Special Features:

In the tests, cleaned injectors were used. The cleaning time in the ultrasound bath in water+10% Superdecontamine (Intersciences, Brussels) at 60° C. was 4 h.

Test Run Times:

The test run time was 12 h without shutdown phases. The one-hour test cycle from CEC F-098-08, shown in FIG. 1, was run through 12 times.

Performance Determination:

The initial power P0,KC [kW] is calculated from the measured torque at full load 4000/min directly after the test has started and the engine has run hot. The procedure is described in Issue 5 of the test procedure (CEC F-98-08). This is done using the same test setup and the PEUGEOT DW10 engine type.

The final performance (Pend,KC) is determined in the 12th cycle in stage 12 (see table, FIG. 1). Here too, the operation point is full load 4000/min. Pend,KC [kW] is calculated from the torque measured.

The power loss in the KC test is calculated as follows:

$$Powerloss, KC\ [\%] = \left(1 - \frac{Pend,\ KC}{P0,\ KC}\right) * 100$$

2.2. DW10 dirty-up clean-up (DU-CU)

The DU-CU test is based on CEC test procedure F-098-08 Issue 5. The procedure is described in Issue 5 of the test procedure (CEC F-98-08). This is done using the same test setup and the PEUGEOT DW10 engine type.

The DU-CU test consists of two individual tests which are run in succession. The first test serves to form deposits (DU), the second to remove the deposits (CU). After the DU, the power loss is determined. After the end of the DU run, the engine is not operated for at least 8 hours and is cooled to ambient temperature. Thereafter, the CU fuel is used to start the CU without deinstalling and cleaning the injectors. The deposits and power loss ideally decline over the course of the CU test.

Change and Special Features:

Cleaned injectors were installed in the engine prior to each DU test. The cleaning time in the ultrasound bath at 60° C., in water+10% Superdecontamine (Intersciences, Brussels), was 4 h.

Test Run Times:

The test run time was 12 h for the DU and 12 h for the CU. The engine was operated in the DU and CU tests without shutdown phases.

The one-hour test cycle from CEC F-098-08, shown in FIG. 1, was run through 12 times in each case.

Performance Determination:

The initial power P0,du [kW] is calculated from the measured torque at full load 4000/min directly after the test has started and the engine has run hot. The procedure is likewise described in Issue 5 of the test procedure.

The final performance (Pend,du) is determined in the 12th cycle in stage 12 (see table above). Here too, the operation point is full load 4000/min. Pend,du [kW] is calculated from the torque measured.

The power loss in the DU is calculated as follows:

$$Powerloss, du\ [\%] = \left(1 - \frac{Pend, du}{P0, du}\right) * 100$$

Clean-up

The initial power P0,cu [kW] is calculated from the measured torque at full load 4000/min directly after the test has started and the engine has run hot in the CU. The procedure is likewise described in Issue 5 of the test procedure.

The final performance (Pend,cu) is determined in the 12th cycle in stage 12 (see table, FIG. 1). Here too, the operation point is full load 4000/min. Pend,cu [kW] is calculated from the torque measured.

The power loss in the CU test is calculated as follows (negative number for the power loss in the cu test means an increase in performance)

$$Powerloss(DU, CU)\ [\%] = \left(\frac{Pend, du - pend, cu}{P0, du}\right) * 100$$

The fuel used was a commercial diesel fuel from Haltermann (RF-06-03). To artificially induce the formation of deposits at the injectors, 1 ppm by weight of zinc in the form of a zinc didodecanoate solution was added thereto.

3. IDID test—determination of additive effect on internal injector deposits

The formation of deposits within the injector was characterized by the deviations in the exhaust gas temperatures of the cylinders at the cylinder outlet on cold starting of the DW10 engine.

To promote the formation of deposits, 1 mg/l of sodium salt of an organic acid, 20 mg/l of dodecenylsuccinic acid and 10 mg/l of water were added to the fuel.

The test is conducted as a dirty-up clean-up test (DU-CU). DU-CU is based on CEC test procedure F-098-08 Issue 5.

The DU-CU test consists of two individual tests which are run in succession. The first test serves to form deposits (DU), the second to remove the deposits (CU).

After the DU run, after a rest phase of at least eight hours, a cold start of the engine is conducted, followed by idling for 10 minutes.

Thereafter, the CU fuel is used to start the CU without deinstalling and cleaning the injectors. After the CU run over 8 h, after a rest phase of at least eight hours, a cold start of the engine is conducted, followed by idling for 10 minutes.

The evaluation is effected by the comparison of the temperature profiles for the individual cylinders after the cold start in the du and CU runs.

The IDID test indicates the formation of internal deposits in the injector. The characteristic used in this test is the exhaust gas temperature of the individual cylinders. In an injector system without IDIDs, the exhaust gas temperatures of the cylinders increase homogeneously. In the presence of IDIDs, the exhaust gas temperatures of the individual cylinders do not increase homogeneously and deviate from one another.

The temperature sensors are beyond the cylinder head outlet in the exhaust gas manifold. Significant deviation of the individual cylinder temperatures (e.g. >20° C.) indicates the presence of internal injector deposits (IDIDs).

The tests (DU and CU) are each conducted with run time 8 h. The one-hour test cycle from CEC F-098-08 is run through 8 times in each case. In the event of deviations of the individual cylinder temperatures of greater than 45° C. from the mean for all 4 cylinders, the test is stopped early.

B. Preparation Examples:

Preparation Example 1

Preparation of polyisobutene epoxide

To a solution of polyisobutene 1000 (300 g) in n-heptane (400 ml) are added, at room temperature, formic acid (96.6 g) and methyltrioctylammonium chloride (1.33 g). The reaction mixture is heated to 75° C. and hydrogen peroxide solution (30%, 88.4 g) is slowly added dropwise, in the course of which the temperature is kept at 75° C. The reaction mixture is stirred at 75° C. for 10 h and cooled to room temperature, and the phases are separated. The organic phase is washed successively with aqueous $NaHSO_3$ solution, saturated $NaHCO_3$ solution and water. The organic phase is dried over $Na_2SO_4$ and the solvent is removed under reduced pressure with the aid of a rotary evaporator. This gives polyisobutene epoxide (285 g).

Preparation Example 2 polyisobutene epoxide Quaternized with N-methylpyrrolidine/acetic Acid

Polyisobutene epoxide from preparation example 1 (30 g) is admixed with methanol (36.1 g), and N-methylpyrrolidine (4.5 g) and acetic acid (1.6 g) are added. The reaction mixture is transferred into an autoclave, inertized with nitrogen and stirred under autogenous pressure at 140° C. for 20 h. The reactor contents are discharged and volatile constituents are removed under reduced pressure with the aid of a rotary evaporator. A MALDI-MS analysis of the reaction product thus obtained confirms the formation of the quaternary ammonium compound.

Preparation Example 3

1-dodecene oxide Quaternized with N-methylpyrrolidine/acetic Acid

A solution of 1-dodecene oxide (73.7 g) and N-methylpyrrolidine (97.2 g) in isopropanol (193.7 g) is admixed at 60° with acetic acid (22.8 g) within 10 minutes, and the reaction mixture thus obtained is stirred at 60° C. for 14 h. Volatile constituents are removed under reduced pressure with the aid of a rotary evaporator. A $^1$H NMR analysis (CDCl$_3$) of the reaction product thus obtained (124 g) confirms the formation of the quaternary ammonium compound (δ(NCH$_3$)=3.30 ppm).

Preparation Example 4

Mixture of 1-dodecene oxide, 1-tetradecene oxide and 1-hexadecene oxide, Quaternized with N-methylpyrrolidine/acetic Acid A solution of 1-dodecene oxide (18.4 g), 1-tetradecene oxide (21.2 g), 1-hexadecene oxide (24.0 g) and N-methylpyrrolidine (51.1 g) in isopropanol (133 g) is admixed at 60° with acetic acid (18.0 g) within 10 minutes, and the reaction mixture obtained is stirred at 60° C. for 15 h. Volatile constituents are removed under reduced pressure with the aid of a rotary evaporator. A $^1$H NMR analysis (CDCl$_3$) of the reaction product thus obtained (102 g) confirms the formation of the quaternary ammonium compound (δ(NCH$_3$)=3.30 ppm).

Preparation Example 5

1-dodecene oxide Quaternized with NMe$_3$/Tall Oil Fatty Acid

In an autoclave, a solution of 1-dodecene oxide (19.4 g) in isopropanol (59.4 g) is admixed at room temperature with trimethylamine (11.8 g). The mixture is heated to 60° C. under autogenous pressure, and tall oil fatty acid (28.2 g) is metered in slowly and rinsed in with isopropanol (10 ml). The reaction mixture is stirred at 60° C. for a further 12 h. The reactor contents are cooled and volatile constituents are driven out with a nitrogen stream. The solvent is subsequently removed under reduced pressure with the aid of a rotary evaporator. A $^1$H NMR analysis (CDCl$_3$) of the reaction product thus obtained (53.4 g) confirms the formation of the quaternary ammonium compound (δ(N(CH$_3$)$_3$)= 3.40 ppm).

Preparation Example 6

1-dodecene oxide Quaternized with N,N-dimethylethanolamine/Tall Oil Fatty Acid

A solution of 1-dodecene oxide (73.6 g) and N,N-dimethylethanolamine (34.2 g) in isopropanol (214.8 g) is admixed at 60° C. with tall oil fatty acid (107 g) within 20 minutes, and the reaction mixture thus obtained is stirred at 60° C. for 22 h. Volatile constituents are removed under reduced pressure with the aid of a rotary evaporator. A $^1$H NMR analysis (CDCl$_3$) of the reaction product thus obtained (212 g) confirms the formation of the quaternary ammonium compound (N(CH$_3$)$_a$)=3.33 ppm, N(CH$_3$)$_b$)=3.34 ppm).

Preparation Example 7

1-dodecene oxide Quaternized with NMe$_3$/salicylic Acid

In an autoclave, a solution of 1-dodecene oxide (23.9 g) in isopropanol (57.1 g) is admixed at room temperature with trimethylamine (15.3 g). The mixture is heated to 60° C. under autogenous pressure, and a solution of salicylic acid (17.9 g) in isopropanol (40 g) is metered in slowly and rinsed in with isopropanol (10 ml). The reaction mixture is stirred at 60° C. for a further 12 h. The reactor contents are cooled and volatile constituents are driven out with a nitrogen stream. The solvent is subsequently removed under reduced pressure with the aid of a rotary evaporator. A $^1$H NMR analysis (CDCl$_3$) of the reaction product thus obtained (47.5 g) confirms the formation of the quaternary ammonium compound (N(CH$_3$)$_3$)=3.26 ppm).

Preparation Example 8

1-dodecene Oxide Quaternized with N,N-dimethylethanolamine/Salicylic Acid

A solution of 1-dodecene oxide (73.6 g) and N,N-dimethylethanolamine (34.2 g) in isopropanol (160.3 g) is admixed at 60° C. with salicylic acid (52.4 g) within 20 minutes, and the reaction mixture thus obtained is stirred at 60° C. for 23 h. Volatile constituents are removed under reduced pressure with the aid of a rotary evaporator. A $^1$H NMR analysis (CDCl$_3$) of the reaction product thus obtained (154 g) confirms the formation of the quaternary ammonium compound (N(CH$_3$)$_a$)=3.21 ppm, N(CH$_3$)$_b$)=3.22 ppm).

C. Use Examples:

In the use examples which follow, the additives are used either as a pure substance (as synthesized in the above preparation examples) or in the form of an additive package.

Use Example 1

Determination of Additive Action on the Formation of Deposits in Diesel Engine Injection Nozzles a) XUD9 Tests The results are summarized in Table 1.

TABLE 1

Results of the XUD9 tests

| Ex. Reference | Fuel | Dosage ppm active | Flow restriction 0.1 mm needle stroke [%] |
|---|---|---|---|
| #1 according to preparation example 3 | EN590-B7-1 | 40 | 14.3 |
| #2 base value | EN590-B7-1 | 0 | 72.5 |
| #3 according to preparation example 3 | RF-06-03 | 60 | 52.9 |
| #4 base value | RF-06-03 | 0 | 77.2 |
| #5 according to preparation example 4 | EN590-B7-1 | 40 | 7 |
| #6 according to preparation example 5 | EN590-B7-2 | 40 | 1.5 |
| #7 base value | EN590-B7-2 | 0 | 73.2 |
| #8 according to preparation example 2 | RF-06-03 | 40 | 0 |
| #9 base value | RF-06-03 | 0 | 68 |

EN590-B7-1 and -2 are commercial diesel fuels to EN590 with maximum biodiesel content 7% to DIN EN 14214.

b) DW10 Dirty-up Clean-up Test

TABLE 2

Results of the DW10 DU CU tests

| Ex. Reference | Fuel | Dosage ppm active | % power loss DU, see description | % power loss DU-CU, see description |
|---|---|---|---|---|
| #1 according to preparation example 4 | RF-06-03 | 105 | 4.1 | −6.1 |

Explicit reference is made to the disclosure of the publications cited herein.

The invention claimed is:
1. A reaction product comprising a quaternized nitrogen compound, obtained by a process comprising:
reacting i) at least one hydrocarbyl epoxide of formula I:

(I)

wherein at least one of $R_1$ and $R_2$ is a straight-chain or branched, saturated or unsaturated, hydrocarbyl radical having 7 to 50 carbon atoms and the other of the two radicals is optionally H or a straight-chain or branched $C_1$-$C_7$-alkyl or $C_2$-$C_7$- alkenyl, optionally interrupted by one or more heteroatom groups, or optionally mono- or polysubstituted; and
$R_3$ and $R_4$ are each independently H or a hydrocarbyl radical as defined for $R_1$ and $R_2$ above;
with ii) at least one tertiary amine of formula II:

(II)

wherein $R_a$ $R_b$ and $R_c$ are each independently a straight-chain or branched, saturated or unsaturated, optionally substituted hydrocarbyl radical, or two of $R_a$, $R_b$ and $R_c$ together with the nitrogen atom to which they are bonded, form an optionally substituted 5- to 7-membered, saturated or unsaturated, nonaromatic or aromatic heterocyclic ring which may optionally bear at least one further ring heteroatom selected from O, S or N;
in the presence of iii) at least one acid of formula III:

(III)

in which $A^-$ is the anion of at least one of an inorganic acid and an organic acid selected from the group consisting of $C_1$-$C_4$ monocarboxylic acids, aromatic carboxylic acids, caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid, behenic acid, lignoceric acid, cerotic acid, melissic acid, monounsaturated fatty acids, diunsaturated fatty acids, triunsaturated fatty acids, tetra- and polyunsaturated fatty acids, ricinoleic acid, gondoic acid, nervonic acid, vernolic acid, malvalic acid, chaulmoogric acid and tall oil fatty acids.

2. The reaction product according to claim 1, which comprises at least one quaternized nitrogen compound of formula (IV):

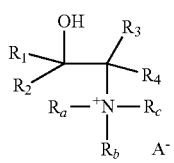

(IV)

wherein $R_1$, $R_2$, $R_3$, $R_4$, $R_a$, $R_b$, and $R_c$ are each as defined and A is the anion of an organic acid.

3. The reaction product according to claim 2, wherein the acid is selected from the group consisting of $C_1$-$C_4$ monocarboxylic acids, aromatic carboxylic acids and fatty acids selected from straight-chain or branched, monounsaturated or polyunsaturated, optionally substituted $C_6$-$C_{30}$ monocarboxylic acids.

4. The reaction product according to claim 1, wherein the reaction product comprises at least one compound of formula IV:

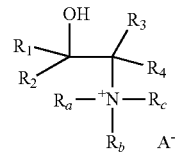

(IV)

wherein $R_1$, $R_2$, $R_3$, $R_4$, $R_a$, $R_b$, and $R_c$ are each as defined and A is the anion selected from the group consisting of a $C_1$-$C_4$ monocarboxylic acid and an aromatic carboxylic acids.

5. The reaction product according to claim 1, wherein the amine of formula II is selected from tri-$C_1$-$C_{24}$-alkylamines or compounds in which one of the $R_a$, $R_b$ and $R_c$ radicals is a $C_1$-$C_4$-alkyl radical and the two other radicals, together with the nitrogen atom to which they are bonded, form a 5- or 6-membered heterocyclic saturated or unsaturated ring which may optionally bear at least one further ring heteroatom selected from the group consisting of O, S and N.

6. The reaction product according to claim 1, wherein the polyalkylene is a polyisobutylene having a proportion of vinylidene double bonds of greater than 70 mol %.

7. The reaction product according to claim 1, wherein the hydrocarbyl radical of $R_1$ or $R_2$ is a straight-chain or branched aliphatic hydrocarbyl radical having 8 to 40 carbons.

8. A method for reducing deposits in an intake system of a DISI (Direct Injection Spark ignition) or PFI (port fuel injector) engine or other gasoline engine comprising:
contacting said engine with a reaction product comprising a quaternized nitrogen compound, or with a fraction thereof which comprises a quaternized nitrogen compound, which is obtained by a process comprising:
reacting i) at least one hydrocarbyl epoxide of formula I:

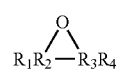

(I)

wherein at least one of $R_1$ and $R_2$ is a straight-chain or branched, saturated or unsaturated, hydrocarbyl radical having 7 to 50 carbon atoms and the other of the two radicals is optionally H or a straight-chain or branched $C_1$-$C_7$-alkyl or $C_2$-$C_7$ alkenyl, optionally interrupted by one or more heteroatom groups, or optionally mono- or polysubstituted, and
$R_3$ and $R_4$ are each independently H or a hydrocarbyl radical as defined for $R_1$ and $R_2$ above;
with ii) at least one tertiary amine of formula II:

(II)

wherein $R_a$ $R_b$ and $R_c$ are each independently a straight-chain or branched, saturated or unsaturated, optionally substituted hydrocarbyl radical, or two of $R_a$, $R_b$ and $R_c$ together with the nitrogen atom to which they are bonded, form an optionally substituted 5- to 7-membered, saturated or unsaturated, nonaromatic or aromatic heterocyclic ring which may optionally bear at least one further ring heteroatom selected from O, S or N;

in the presence of iii) at least one acid of formula III:

$$H^+A^- \quad \text{(III)}$$

in which $A^-$ is the anion of at least one mono- or poly-basic, inorganic or organic, natural or synthetic acid.

9. A method for reducing and/or preventing deposits in an intake system and/or for reducing valve sticking in direct injection diesel engines comprising:

contacting said engine with a reaction product comprising a quaternized nitrogen compound, or with a fraction thereof which comprises a quaternized nitrogen compound, which is obtained by purification of a reaction product obtained by a process comprising:

reacting i) at least one hydrocarbyl epoxide of formula I:

(I)

wherein at least one of $R_1$ and $R_2$ is a straight-chain or branched, saturated or unsaturated, hydrocarbyl radical having 7 to 50 carbon atoms and the other of the two radicals is optionally H or a straight-chain or branched $C_1$-$C_7$-alkyl or $C_2$-$C_7$ alkenyl, optionally interrupted by one or more heteroatom groups, or optionally mono- or polysubstituted; and $R_3$ and $R_4$ are each independently H or a hydrocarbyl radical as defined for $R_1$ and $R_2$ above;

with ii) at least one tertiary amine of formula II:

$$R_aR_bR_cN \quad \text{(II)}$$

wherein $R_a$, $R_b$ and $R_c$ are each independently a straight-chain or branched, saturated or unsaturated, optionally substituted hydrocarbyl radical, or two of $R_a$, $R_b$ and $R_c$ together with the nitrogen atom to which they are bonded, form an optionally substituted 5- to 7-membered, saturated or unsaturated, nonaromatic or aromatic heterocyclic ring which may optionally bear at least one further ring heteroatom selected from O, S or N;

in the presence of iii) at least one acid of formula (III):

$$H^+A^- \quad \text{(III)}$$

in which $A^-$ is the anion of at least one mono- or poly-basic, inorganic or organic, natural or synthetic acid.

10. A gasoline fuel additive comprising the reaction product according to claim 1.

11. A diesel fuel additive comprising the reaction product according to claim 1.

12. A method of reducing the fuel consumption of direct injection diesel engines and/or for minimizing power loss in direct injection diesel engines, said method comprising:

contacting the engine with a reaction product comprising a quaternized nitrogen compound, said reaction product being obtained by:

reacting i) at least one hydrocarbyl epoxide of formula I:

(I)

wherein at least one of $R_1$ and $R_2$ is a straight-chain or branched, saturated or unsaturated, hydrocarbyl radical having 7 to 50 carbon atoms and the other of the two radicals is optionally H or a straight-chain or branched $C_1$-$C_7$-alkyl or $C_2$-$C_7$-alkenyl, optionally interrupted by one or more heteroatom groups, or optionally mono- or polysubstituted; and $R_3$ and $R_4$ are each independently H or a short-chain hydrocarbyl radical as defined above;

with ii) at least one tertiary amine of formula II:

$$R_aR_bR_cN \quad \text{(II)}$$

wherein $R_a$, $R_b$ and $R_c$ are each independently a straight-chain or branched, saturated or unsaturated, optionally substituted hydrocarbyl radical, or two of $R_a$, $R_b$ and $R_c$ together with the nitrogen atom to which they are bonded, form an optionally substituted 5- to 7-membered, saturated or unsaturated, nonaromatic or aromatic heterocyclic ring which may optionally bear at least one further ring heteroatom selected from O, S or N;

in the presence of iii) at least one acid of formula III:

$$H^+A^- \quad \text{(III)}$$

wherein $A^-$ is the anion of at least one mono- or poly-basic, inorganic or organic, natural or synthetic acid.

13. The method of claim 12, wherein the direct injection diesel engine comprises a common rail injection system.

14. The reaction product according to claim 1, wherein $A^-$ is the anion of an organic acid selected from the group consisting of $C_1$-$C_4$ monocarboxylic acids, aromatic carboxylic acids and tall oil fatty acids.

15. The method according to claim 9 wherein the deposits are internal diesel injector deposits (IDIDs).

16. The method of claim 9, wherein the direct injection diesel engine comprises a common rail injection system.

* * * * *

UNITED STATES PATENT AND TRADEMARK OFFICE
CERTIFICATE OF CORRECTION

| | | |
|---|---|---|
| PATENT NO. | : 10,173,963 B2 | Page 1 of 1 |
| APPLICATION NO. | : 14/436951 | |
| DATED | : January 8, 2019 | |
| INVENTOR(S) | : Markus Hansch et al. | |

It is certified that error appears in the above-identified patent and that said Letters Patent is hereby corrected as shown below:

In the Specification

In Column 1, Line 10, "Europeant" should read -- European --, therefor.

In Column 1, Line 10, "12189538," should read -- 12189538.7, --, therefor.

In Column 15, Lines 63-64, "$C_a$-alkylene" should read -- $C_4$-alkylene --, therefor.

In Column 18, Line 24, "2 to 15" should read -- 3 to 15 --, therefor.

In Column 19, Line 11, "$R^1$" should read -- $R^7$ --, therefor.

In the Claims

In Column 29, Line 24, Claim 1, "$R_a$" should read -- $R_a$, --, therefor.

In Column 30, Line 57, Claim 8, "polysubstituted," should read -- polysubstituted; --, therefor.

In Column 30, Line 63, Claim 8, "$R_a$" should read -- $R_a$, --, therefor.

In Column 31, Line 47, Claim 9, "(III):" should read -- III: --, therefor.

Signed and Sealed this
Fifth Day of May, 2020

Andrei Iancu
*Director of the United States Patent and Trademark Office*